(12) United States Patent
Bleier

(10) Patent No.: US 10,653,745 B2
(45) Date of Patent: *May 19, 2020

(54) TREATMENT OF RHINOSINUSITIS WITH P-GLYCOPROTEIN INHIBITORS

(71) Applicant: Massachusetts Eye and Ear Infirmary, Boston, MA (US)

(72) Inventor: Benjamin S. Bleier, Weston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/687,074

(22) Filed: Aug. 25, 2017

(65) Prior Publication Data

US 2017/0348384 A1 Dec. 7, 2017

Related U.S. Application Data

(63) Continuation of application No. 14/655,662, filed as application No. PCT/US2013/077945 on Dec. 27, 2013, now Pat. No. 9,744,210.

(60) Provisional application No. 61/746,290, filed on Dec. 27, 2012.

(51) Int. Cl.

| | |
|---|---|
| *A61K 31/277* | (2006.01) |
| *A61K 9/00* | (2006.01) |
| *A61K 45/06* | (2006.01) |
| *A61K 31/4164* | (2006.01) |
| *A61K 31/43* | (2006.01) |
| *A61K 31/4545* | (2006.01) |
| *A61K 31/47* | (2006.01) |
| *A61K 31/4725* | (2006.01) |
| *A61K 31/473* | (2006.01) |
| *A61K 31/496* | (2006.01) |
| *A61K 31/545* | (2006.01) |
| *A61K 31/55* | (2006.01) |
| *A61K 31/56* | (2006.01) |
| *A61K 31/573* | (2006.01) |
| *A61K 31/58* | (2006.01) |
| *A61K 31/65* | (2006.01) |
| *A61K 31/7048* | (2006.01) |
| *A61K 38/13* | (2006.01) |
| *A61L 27/54* | (2006.01) |
| *A61L 27/20* | (2006.01) |

(52) U.S. Cl.
CPC ............ *A61K 38/13* (2013.01); *A61K 9/0043* (2013.01); *A61K 31/277* (2013.01); *A61K 31/4164* (2013.01); *A61K 31/43* (2013.01); *A61K 31/4545* (2013.01); *A61K 31/47* (2013.01); *A61K 31/473* (2013.01); *A61K 31/4725* (2013.01); *A61K 31/496* (2013.01); *A61K 31/545* (2013.01); *A61K 31/55* (2013.01); *A61K 31/56* (2013.01); *A61K 31/573* (2013.01); *A61K 31/58* (2013.01); *A61K 31/65* (2013.01); *A61K 31/7048* (2013.01); *A61K 45/06* (2013.01); *A61L 27/20* (2013.01); *A61L 27/54* (2013.01)

(58) Field of Classification Search
CPC .... A61K 31/277; A61K 31/573; A61K 38/12; A61K 38/13
See application file for complete search history.

(56) References Cited

U.S. PATENT DOCUMENTS

| | | |
|---|---|---|
| 2,989,437 A | 6/1961 | Wruble et al. |
| 5,898,037 A | 4/1999 | Marx |
| 6,451,815 B1 | 9/2002 | Hwang |
| 6,503,953 B2 | 1/2003 | Vyden |
| 6,579,898 B2 | 6/2003 | Humphrey |
| 7,115,565 B2 | 10/2006 | Gao |
| 7,544,192 B2 | 6/2009 | Eaton et al. |
| 7,888,049 B2 | 2/2011 | Shaari |
| 7,935,731 B2 | 5/2011 | Davis |

(Continued)

FOREIGN PATENT DOCUMENTS

| | | |
|---|---|---|
| CN | 101380328 | 3/2009 |
| WO | 01/58470 | 8/2001 |

(Continued)

OTHER PUBLICATIONS

Palmeira et al. Three Decades of P-gp Inhibitors: Skimming Through Several Generations and Scaffolds. Current Medicinal Chemistry. 2012, vol. 19, No. 13, pp. 1946-2025. (Year: 2012).*

(Continued)

*Primary Examiner* — Jeffrey E. Russel
(74) *Attorney, Agent, or Firm* — Fish & Richardson P.C.

(57) ABSTRACT

Provided herein are, inter alia, methods for treating rhinosinusitis with P-glycoprotein inhibitors. A subject having rhinosinusitis is identified and then treated by administration to the subject an effective amount of a P-gp inhibitor. The subject having rhinosinusitis can be identified by one of skill in the art based on known methods, e.g., based on detection of the presence of symptoms, by endoscopy, or by computed tomography. The efficacy of the treatment can be monitored by methods known in the art, e.g., by monitoring symptoms, by endoscopy or computed tomography. The P-glycoprotein inhibitor can be delivered to the subject's nasal passage and sinuses by an inhalation device, by flushing, by spraying, or by an eluting implant surgically placed in the subject's nasal passage or sinuses. The P-glycoprotein inhibitor can also be administered in combination with one or both of a corticosteroid and an antibiotic.

21 Claims, 24 Drawing Sheets

(56) References Cited

U.S. PATENT DOCUMENTS

| | | | | |
|---|---|---|---|---|
| 8,003,106 | B2* | 8/2011 | Mikayama | C07K 16/1018 424/159.1 |
| 8,124,091 | B2* | 2/2012 | Kato | C07K 16/1018 424/139.1 |
| 8,357,696 | B2* | 1/2013 | Surber | A61K 9/0073 514/294 |
| 8,637,469 | B2* | 1/2014 | Levitt | A61K 9/0043 514/21.2 |
| 8,980,848 | B2 | 3/2015 | Chan | |
| 9,744,210 | B2* | 8/2017 | Bleier | A61K 38/13 |
| 2005/0245906 | A1 | 11/2005 | Makower | |
| 2006/0051300 | A1 | 3/2006 | Chaudry | |
| 2006/0134009 | A1 | 6/2006 | Deaver et al. | |
| 2007/0015719 | A1 | 1/2007 | Jenkins | |
| 2007/0020299 | A1* | 1/2007 | Pipkin | A61K 9/0078 424/400 |
| 2007/0178526 | A1* | 8/2007 | Kountakis | G01N 33/6803 435/7.1 |
| 2007/0226012 | A1 | 9/2007 | Salgado | |
| 2008/0118925 | A1 | 5/2008 | Cuppens | |
| 2008/0199522 | A1 | 8/2008 | Sawada et al. | |
| 2010/0016267 | A1* | 1/2010 | Theeuwes | A61K 9/0043 514/172 |
| 2010/0129316 | A1 | 5/2010 | Levitt | |
| 2011/0118199 | A1* | 5/2011 | Dormeyer | A61K 31/17 514/34 |
| 2011/0240012 | A1* | 10/2011 | Pilon | A61K 9/0043 128/200.14 |
| 2012/0095019 | A1 | 4/2012 | Sinha | |
| 2012/0219565 | A1 | 8/2012 | Presta | |
| 2012/0240930 | A1 | 9/2012 | Kristensson | |
| 2014/0336463 | A1* | 11/2014 | Shikani | A61M 11/00 600/158 |
| 2015/0017099 | A1* | 1/2015 | Cohen | G01N 33/6893 424/9.1 |

FOREIGN PATENT DOCUMENTS

| | | |
|---|---|---|
| WO | 2005/072704 | 8/2005 |
| WO | 2012/006599 | 1/2012 |
| WO | 2014/106021 | 7/2014 |

OTHER PUBLICATIONS

Al-Massarani et al. In vitro Cytotoxic, Antibacterial and Antiviral Activities of Triterpenes from the Red Sea Sponge, *Siphonochalina siphonella*. Tropical Journal of Pharmaceutical Research. Jan. 2015, vol. 14, No. 1, pp. 33-40. (Year: 2015).*

Aqil et al. Antimicrobial, antioxidant, and antimutagenic activities of selected marine natural products and tobacco cembranoids. Drug and Chemical Toxicology. 2011, vol. 34, No. 2, pp. 167-179. (Year: 2011).*

Jain et al. Reversal of P-Glycoprotein-Mediated Multidrug Resistance by Sipholane Triterpenoids. Journal of Natural Products. 2007, vol. 70, pp. 928-931. (Year: 2007).*

Lopez et al. Marine Natural Products with P-Glycoprotein Inhibitor Properties. Marine Drugs. 2014, vol. 12, pp. 525-546. (Year: 2014).*

Amorim et al., "Nasal eosinophilia: an indicator of eosinophilic inflammation in asthma," Clin Exp Allergy. Jun. 2010; 40(6):867-874. Epub Jan. 20, 2010.

Bachert et al., "*Staphylococcus aureus* enterotoxins: a key in airway disease?" Allergy, Jun. 2002;57(6):480-7.

Bark et al. PSC833, cyclosporine analogue, downregulates MDR1 expression by activating JNK/c-Jun/AP-1 and suppressing NF-kB. Cancer Chemother Pharmacol., May 2010;65(6):1131-1136.

Blackwell et al., "Summary health statistics for U.S. adults: National Health Interview Survey, 1997," Vital Health Stat 10, May 2002;(205):1-109.

Bleier B.S. et al. Regional expression of epithelial MDR1/P-glycoprotein in chronic rhinosinusitis with and without nasal polyposis. Int Forum Allergy & Rhinol., Mar.-Apr. 2012;2(2):122-125.

Bleier et al., "Chitosan glycerophosphate-based semirigid dexamethasone eluting biodegradable stent," Am J Rhinol Allergy, 23(1):76-79, Jan./Feb. 2009.

Cervin et al., Effects of long-term clarithromycin treatment on lavage-fluid markers of inflammation in chronic rhinosinusltis. Clinical Physiology and Functional Imaging, 2009, vol. 29, No. 2, pp. 136-142.

Chin et al., "Nasal polyposis: an inflammatory condition requiring effective anti-inflammatory treatment," Curr Opin Otolaryngol Head Neck Surg, Feb. 2013;21(1):23-30.

Cho et al., "Impact of chronic rhinosinusitis and endoscopic sinus surgery on bone remodeling of the paranasal sinuses," Am J Rhinol, Sep.-Oct. 2008;22(5):537-541.

Damm et al., "Proinflammatory effects of *Staphylococcus aureus* exotoxin B on nasal epithelial cells," Otolaryngol Head Neck Surg. Feb. 2006;134(2):245-9.

Detwiller et al., "Steroid-independent upregulation of matrix metalloproteinase 9 in chronic rhinosinusitis patients with radiographic evidence of osteitis," Int Forum Allergy Rhinol. May 2013;3(5):364-368, Epub Feb. 8, 2013.

Drach et al., "Involvement of P-glycoprotein in the transmembrane transport of interleukin-2 (IL-2), IL-4, and interferon-gamma in normal human T lymphocytes," Blood. Sep. 1996; 88(5):1747-54.

Drori et al., "Potentiation of anticancer-drug cytotoxicity by multidrug-resistance chemosensitizers involves alterations in membrane fluidity leading to increased membrane permeability," Eur J Biochem. Mar. 1995; 228:1020-9.

Ehrhardt et al., "16HBE14o—human bronchial epithelial cell layers express P-glycoprotein, lung resistance-related protein, and caveolin-1," Pharm. Res. Apr. 2003; 20(4):545-51.

Erbek et al., "The role of allergy in the severity of nasal polyposis," Am J Rhinol, 21(6): 686-90, 2007, abstract.

European Search Report in Application No. 13866961.9-1466/2938339 dated Jun. 6, 2016, 7 pages.

Ferguson, "Categorization of eosinophilic chronic rhinosinusitis," Curr Opin Otolaryngol Head Neck Surg. Jun. 2004;12(3):237-242.

Fernandez et al., "Influence of the pro-inflammatory cytokines on P-glycoprotein expression and functionality," J Pharm. Pharm. Sci. Nov. 17, 2004; 7(3):359-71.

Fokkens et al., "EPOS 2012: European position paper on rhinosinusitis and nasal polyps 2012. A summary for otorhinolaryngologists," Rhinology, Mar. 2012; 50(1):1-12.

Georgalas et al., "Global Osteitis Scoring Scale and chronic rhinosinusitis: a marker of revision surgery," Clin Otolaryngol, Dec. 2010;35(6):455-461.

Georgalas, "Osteitis and paranasal sinus inflammation: what we know and what we do not," Curr Opin Otolaryngol Head Neck Surg, Feb. 2013;21(1):45-49.

Golden et al., "Blood-brain barrier efflux transport," J Pharm Sci. Sep. 2003;92(9):1739-53.

Han et al., "Predictors of bronchial hyperresponsiveness in chronic rhinosinusitis with nasal polyp," Allergy, Jan. 2009; 64(1):118-22, Epub Dec. 17, 2008.

Hopkins et al., "The Lund-Mackay staging system for chronic rhinosinusitis: how is it used and what does it predict?," Otolaryngol Head Neck Surg. Oct. 2007;137(4):555-61.

International Preliminary Report on Patentability in International Application No. PCT/US2013/077945, dated Jul. 9, 2015, 6 pages.

International Search Report and Written Opinion in International Application No. PCT/US2013/077945, dated Apr. 29, 2014, 7 pages.

Iqbal et al., "Corticosteroid regulation of P-glycoprotein in the developing blood-brain barrier," Endocrinology, Mar. 2011;152(3):1067-79, Epub Jan. 14, 2011.

Kirkeby et al., "Quantitative immunohistochemistry of fluorescence labelled probes using low-cost software," J Immunol. Methods. Jun. 2005; 301(1-2):102-13.

Kooij et al., "P-glycoprotein acts as an immunomodulator during neuroinflammation," PLoS One. Dec. 8, 2009; 4(12):e8212.

Kopriva et al., "The anti-inflammatory effects of inhaled corticosteroids versus anti-leukotrienes on the lymphocyte P-glycoprotein (PGP) expression in asthmatic children," J Asthma. May 2009;46(4):366-70.

(56) References Cited

OTHER PUBLICATIONS

Lalaker et al. "Chitin stimulates expression of acidic mammalian chitinase and eotaxin-3 by human sinonasal epithelial cells in vitro," Am J Rhinol Allergy, Jan.-Feb. 2009; 23(1):8-14.

Lane et al., "Altered expression of genes associated with innate immunity and inflammation in recalcitrant rhinosinusitis with polyps," Am J Rhinol. Mar.-Apr. 2006;20(2):138-44.

Lee et al., "Risk factors for protracted sinusitis in pediatrics after endoscopic sinus surgery," Auris Nasus Larynx. Dec. 2009;36(6):655-60, Epub May 2, 2009.

Lee et al., "The incidence of concurrent osteitis in patients with chronic rhinosinusitis: a clinicopathological study," Am J Rhinol. May-Jun. 2006;20(3):278-82.

Marty et al., "ATP binding cassette transporter ABC1 is required for the release of interleukin-1beta by P2X7-stimulated and lipopolysaccharide-primed mouse Schwann cells," Glia. Mar. 2005;49(4):511-9.

Mehta et al., "Blood and sputum eosinophil levels in asthma and their relationship to sinus computed tomographic findings," Mayo Clin Proc. Jun. 2008, 83(6):671-8.

Mjösberg et al., "Human IL-25- and IL-33-responsive type 2 innate lymphoid cells are defined by expression of CRTH2 and CD161," Nat Immunol. Sep. 11, 2011;12(11):1055-62.

Morjani et al., "Immunosuppressors as multidrug resistance reversal agents," Methods Mol Biol. 2010;596:433-46.

Newman et al., "Chronic sinusitis. Relationship of computed tomographic findings to allergy, asthma, and eosinophilia," JAMA. Feb. 2, 1994;271(5):363-7.

Nickel, "The mystery of nonclassical protein secretion. A current view on cargo proteins and potential export routes," Eur J Biochem. May 2003;270(10):2109-19.

Olze et al., "Eosinophilic nasal polyps are a rich source of eotaxin, eotaxin-2 and eotaxin-3," Rhinology. Jun. 2006; 44(2):145-50.

Peters et al., "Evidence for altered activity of the IL-6 pathway in chronic rhinosinusitis with nasal polyps," J Allergy Clin Immunol. Feb. 2010;125(2):397-403.

Piccirillo et al., "Psychometric and clinimetric validity of the 20-Item Sino-Nasal Outcome Test (SNOT-20)," Otolaryngol Head Neck Surg. Jan. 2002;126(1):41-7.

Quintanilla-Dieck, et al., "Comparison of disease-specific quality-of-life instruments in the assessment of chronic rhinosinusitis," International Forum of Allergy & Rhinology Nov. 2012;2(6):437-43.

Reh et al., "Treatment-recalcitrant chronic rhinosinusitis with polyps is associated with altered epithelial cell expression of interleukin-33," Am J Rhinol Allergy. Mar.-Apr. 2010;24(2):105-9.

Rosenfeld et al., "Clinical practice guideline: adult sinusitis," Otolaryngol Head Neck Surg. Sep. 2007;137(3 Suppl):S1-31.

Ryan, et al., "Correlations between symptoms, nasal endoscopy, and in-office computed tomography in post-surgical chronic rhinosinusitis patients," Laryngoscope. Mar. 2011;121(3):674-8.

Sachse et al., "*Staphylococcus aureus* invades the epithelium in nasal polyposis and induces IL-6 in nasal epithelial cells in vitro," Allergy. Nov. 2010;65(11):1430-7.

Secher et al., Intranassal Verapamil in Allergen-Induced Rhinitis. Allergy/ 1983, vol. 38, pp. 565-570.

Shapiro, et al., "Effect of quercetin on Hoechst 33342 transport by purified and reconstituted P-glycoprotein," Biochem Pharmacol. Feb. 21, 1997;53(4):587-96.

Snidvongs et al., "Correlation of the Kennedy Osteitis Score to clinico-histologic features of chronic rhinosinusitis," Int Forum Allergy Rhinol. May 2013;3(5):369-75.

Snidvongs et al., "Osteitic bone: a surrogate marker of eosinophilia in chronic rhinosinusitis," Rhinology. Sep. 2012;50(3):299-305.

Soler et al., "Impact of mucosal eosinophilia and nasal polyposis on quality-of-life outcomes after sinus surgery," Otolaryngol Head Neck Surg. Jan. 2010;142(1):64-71.

Soler et al., "Relationship between clinical measures and histopathologic findings in chronic rhinosinusitis," Otolaryngol Head Neck Surg. Oct. 2009;141(4):454-61.

Stein et al., "Modulation of mdr1 expression by cytokines in human colon carcinoma cells: an approach for reversal of multidrug resistance," Br J Cancer. Nov. 1996;74(9):1384-91.

Sun et al., "Clinical significance of eosinophilic cationic protein levels in nasal secretions of patients with nasal polyposis," Eur Arch Otorhinolaryngol. Jul. 2009;266(7):981-6.

Szucs et al., "Eosinophilia in the ethmoid mucosa and its relationship to the severity of inflammation in chronic rhinosinusitis," Am J Rhinol. May-Jun. 2002;16(3):131-4.

Takeno et al., "Pathological mechanisms and clinical features of eosinophilic chronic rhinosinusitis in the Japanese population," Allergol Int. Sep. 2010;59(3):247-56.

Van Crombruggen et al., "Pathogenesis of chronic rhinosinusitis: inflammation," J Allergy Clin Immunol. Oct. 2011;128(4):728-32.

Varma et al., "RP-glycoprotein inhibitors and their screening: a perspective from bioavailability enhancement," Pharmacological Research. Oct. 2003;48(4):347-59.

Wanek T. et al. A comparative small-animal PET evaluation of ["C]tariquidar, ["C]elacridar and (R)-["C]verapamil for detection of P-glycoprotein-expressing murine breast cancer. Eur J Nucl Med Mol Imaging., Jan. 2012;39(1):149-159.doi: 10.1007/s00259-011-1941-7, pp. 1-17.

Wisniewski et al., "Novel cytokines and cytokine-producing T cells in allergic disorders," Allergy Asthma Proc. Mar.-Apr. 2011;32(2):83-94.

Zadeh et al., "Significance of eosinophilia in chronic rhinosinusitis," Am J Rhinol. Nov.-Dec. 2002;16(6):313-7.

Beier, "Regional Expression of Epithelial MDR1/P-gp in Chronic Sinusitis with and without Nasal Polyposis," Abstract of Presentation at Proceedings of the 57th Annual Meeting of the American Rhinologic Society, San Francisco, CA, Sep. 10, 2011, p. 71-72, 3 pages.

Bleier & Feldman, "Corticosteroid Sensitivity of Epithelial MDR1/P-gp in Chronic Sinusitis with Nasal Polyps," Abstract of Presentation at Proceedings of the 58th Annual Meeting of the American Rhinologic Society, Washington, DC, Sep. 8, 2012, p. 32, 2 pages.

* cited by examiner

FIG. 2A
CRSwNP
FIG. 2B
CRS
FIG. 2C
Control
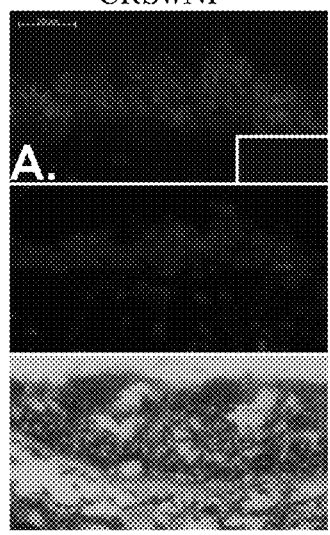
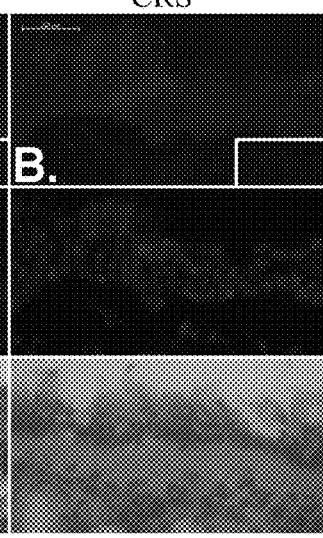
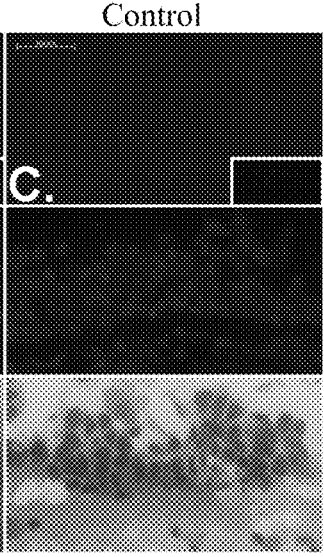

FIG. 3A
FIG. 3B
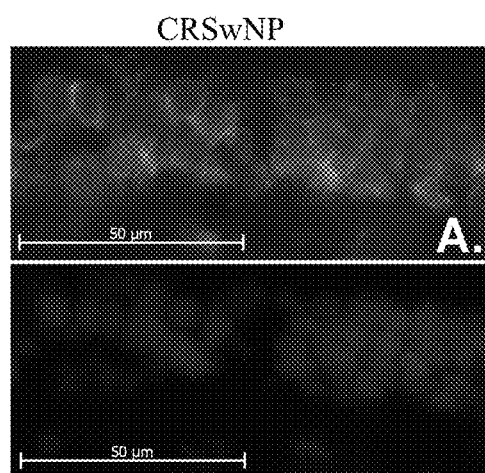
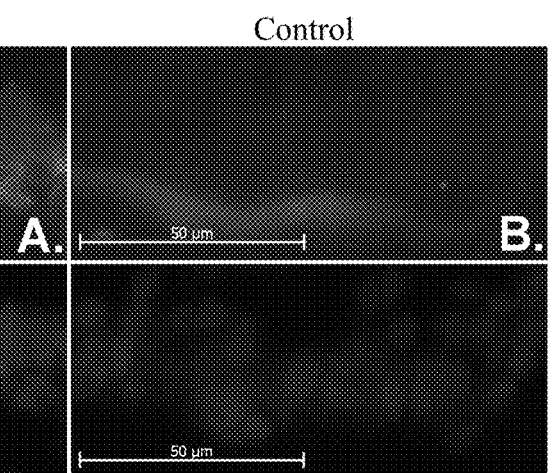

FIG. 13A
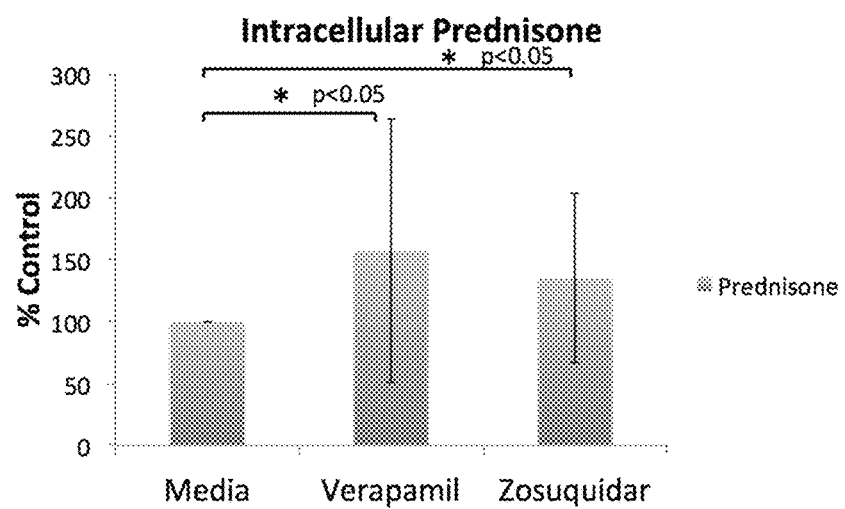
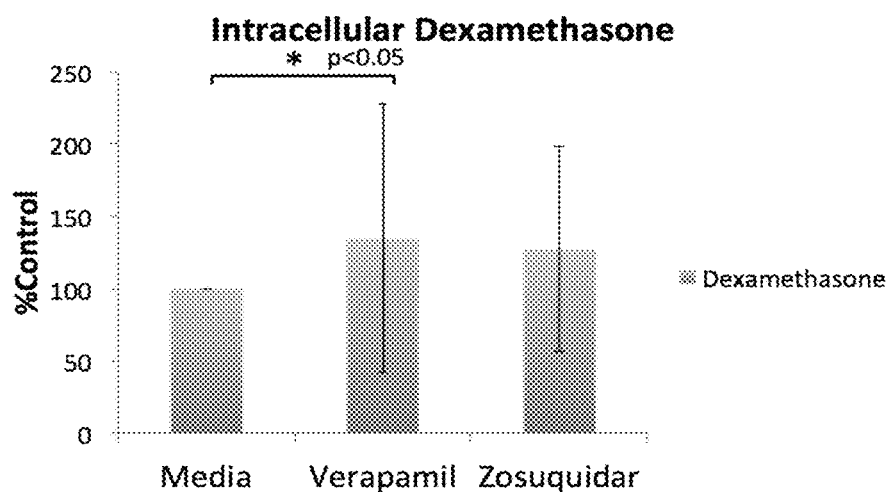
FIG. 13B

FIG. 19A
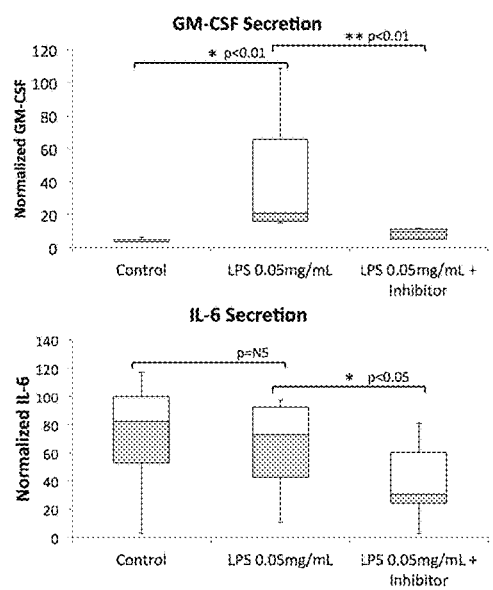
FIG. 19B
FIG. 19C
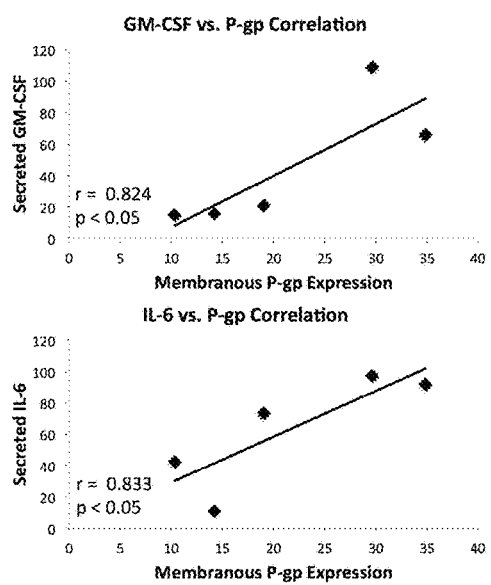
FIG. 19D

FIG. 23A
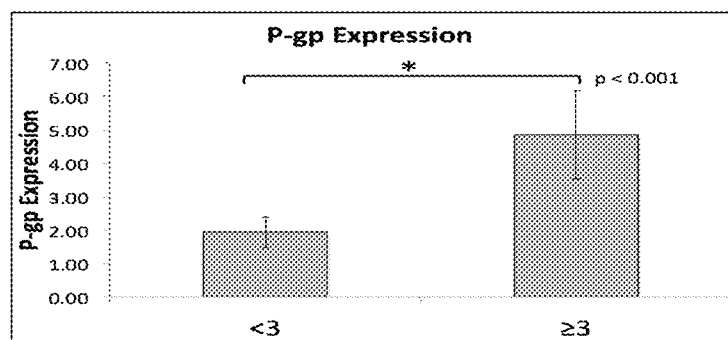
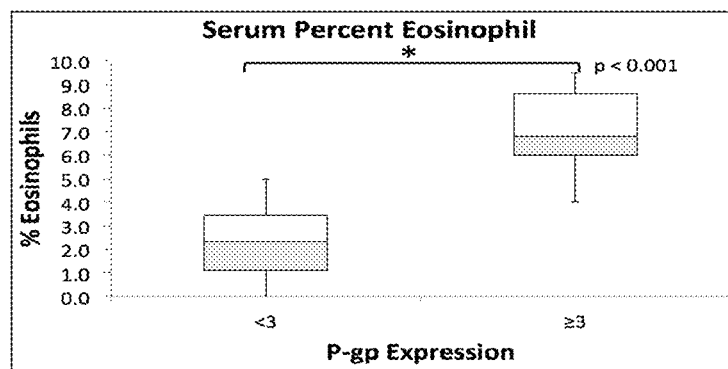
FIG. 23B

TREATMENT OF RHINOSINUSITIS WITH P-GLYCOPROTEIN INHIBITORS

CLAIM OF PRIORITY

This application is a continuation of U.S. patent application Ser. No. 14/655,662, filed on Jun. 25, 2015, which is a 371 U.S. National Application of PCT/US2013/077945, filed on Dec. 27, 2013, which claims the benefit of U.S. Provisional Patent Application Ser. No. 61/746,290, filed on Dec. 27, 2012, the entire contents of which are hereby incorporated by reference.

TECHNICAL FIELD

This invention relates to treatment of rhinosinusitis in a subject, and more particularly to methods for treating rhinosinusitis in a subject with P-glycoprotein inhibitors.

BACKGROUND

Paranasal sinuses are four pairs of air-filled cavities connecting to the nasal passage. The paranasal sinuses are named after the cranial bones in which they are located: the frontal sinuses, the maxillary sinuses, the ethmoid sinuses, and the sphenoid sinuses. A membrane lining the paranasal sinuses secretes mucus, which drains into the nasal passage through a small channel in each sinus. Healthy sinuses are sterile and contain no bacteria. In contrast, the nasal passage normally contains many bacteria that enter through the nostrils as a person breathes.

A number of factors and processes are involved in maintaining healthy sinuses. The mucus secreted by the membrane lining must be fluid but sticky, in order to flow freely yet absorb pollutants and entrap bacteria. It must also contain sufficient amounts of bacteria-fighting substances such as antibodies. Additionally, small hair-like projections called cilia, located in the nostril, must beat in unison to propel mucus outward, in order to expel bacteria and other particles. Moreover, the mucous membranes themselves must be intact, and the sinus passages must be open to allow drainage and the circulation of air through the nasal passage. When one or more of these processes or factors are amiss, causing obstruction of the sinus passage, an infection called sinusitis develops.

Sinusitis is an inflammation of the mucous membrane lining one or more paranasal sinuses. Rhinitis is an inflammation of the mucous membrane lining the nasal passage. Rhinitis and sinusitis usually coexist and are concurrent in most individuals; thus most guidelines and experts now have adopted the term rhinosinusitis (Fokkens et al., Rhinology 2012 March; 50 (Suppl 23): S5).

The symptoms of rhinosinusitis include nasal congestion and obstruction, colored nasal discharge, anterior or posterior nasal drip. Subjects may also experience facial pain or pressure, and in severe cases, suffer a reduction or a loss of smell (Fokkens et al., 2012). There are two different types of rhinosinusitis: acute and chronic. Acute rhinosinusitis is characterized as rhinosinusitis with complete resolution of symptoms within 12 weeks, while chronic rhinosinusitis lasts longer than 12 weeks, and usually involves tissue damage (Fokkens et al., 2012). Nasal polyps are frequently present in some subjects with chronic rhinosinusitis based on epidemiologic studies.

SUMMARY

Disclosed herein are, inter alia, methods for treating rhinosinusitis with P-glycoprotein inhibitors.

In some embodiments, a subject having rhinosinusitis is identified and treated by administration to the subject an effective amount of a P-gp inhibitor. The subject having rhinosinusitis may be identified by one of skill in the art based on known methods, e.g., based on detection of the presence of symptoms, by endoscopy, or by computed tomography. The efficacy of the treatment may be monitored by methods known in the art, e.g., by monitoring symptoms, by endoscopy or computed tomography.

In one aspect, a subject with rhinosinusitis is treated with a P-gp inhibitor in an amount sufficient to inhibit P-gp expression and/or activity. The P-gp inhibitor could be a first generation compound, e.g. verapamil, cyclosporin A, antihypertensive, reserpine, quinidine or yohimbine, tamoxifen, or toremifena. Preferably, the P-gp inhibitor is a second or third generation compound, e.g. PSC 833, R-verapamil, VX-710, GF120918, MS-209, R101933, LY335979, OC144093, XR9051, or XR9576.

In another aspect, a subject with rhinosinusitis is treated with a P-gp inhibitor in an amount sufficient to decrease P-gp expression in the subject's sinonasal epithelial cells, either transcriptionally or posttranscriptionally.

In some embodiments, the P-gp inhibitor is administered systemically. In other embodiments, the P-gp inhibitor is administered locally to the subject's nasal passage and sinuses by an inhalation device, by flushing, spraying, irrigation, nebulization, atomization, or a drug eluting vehicle.

In some embodiments, a subject with rhinosinusitis is treated with a P-gp inhibitor in combination with other conventional treatments, e.g., drugs such as corticosteroids and/or antibiotics, to potentiate the effect of treatment.

In some embodiments, when a subject with rhinosinusitis has nasal polyps, surgical removal of such nasal polyps can be performed in addition to administration of a P-gp inhibitor to the subject. Thus, a subject with rhinosinusitis may undergo both surgery and treatment with a P-gp inhibitor.

In some embodiments, a subject with rhinosinusitis has eosinophilic sinusitis and/or other forms of mucosal inflammation.

In some embodiments, a subject continues to experience symptoms of chronic sinusitis after a sinus surgery, and a P-gp inhibitor-eluting implant, stent, or spacer is used to maintain sinus patency in the subject. The P-gp inhibitor eluting device can be made from bioabsorbable material so that the implant will be absorbed within a short period of time after the implantation and no surgical removal of the implant is necessary. The P-gp inhibitor eluting device can be in the form of solid, semisolid, gel, polymer, or particle.

In some embodiments, the P-glycoprotein inhibitor is administered in combination with one of both of a corticosteroid and/or an antibiotic. The corticosteroid can be, e.g., selected from dexamethasone, prednisone, prednisolone, triamcinolone, cortisol, budesonide, mometasone, fluticasone, flunisolide, and betamethasone. The antibiotic can be, e.g., selected from erythromycin, doxycycline, tetracycline, penicillin, beta-lactam, macrolide, fluoroquinolone, cephalosporin, and sulfonamide.

In some embodiments, a kit for treating rhinosinusitis in a subject is provided. Such a kit comprises a pharmaceutical composition comprising an effective amount of a P-gp inhibitor, and a device for delivering the pharmaceutical composition to the subject's nasal passage and sinuses. The device may deliver the pharmaceutical composition to the subject's nasal passage and sinuses in a liquid or an aerosolized form. In some embodiments, the kit also includes a corticosteroid and/or an antibiotic, in the same pharmaceutical composition as the P-gp inhibitor or in a separate composition.

As used herein, "treatment" means any manner in which one or more of the symptoms of a disease or disorder are ameliorated or otherwise beneficially altered. As used herein, amelioration of the symptoms of a particular disorder refers to any lessening, whether permanent or temporary, lasting or transient that can be attributed to or associated with treatment by the compositions and methods of the present disclosure.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

The term "subject" is used throughout the specification to describe an animal, human or non-human, to whom treatment according to the methods of the present invention is provided. Veterinary and non-veterinary applications are contemplated. The term includes, but is not limited to, mammals, e.g., humans, other primates, pigs, rodents such as mice and rats, rabbits, guinea pigs, hamsters, cows, horses, cats, dogs, sheep and goats. Typical subjects include humans, farm animals, and domestic pets such as cats and dogs.

The term "rhinosinusitis" as used herein includes acute and chronic rhinosinusitis, either with or without the presence of nasal polyps.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 2A-C are a set of matched photomicrograph images (bar=100 μm) of sinus tissue representing P-gp immunostaining (top panel), propidium iodide nuclear stain (middle panel), and H&E staining (lower panel) in CRSwNP (A), CRS (B), and Control (C) subjects. Note the increased P-gp epithelial staining in the CRSwNP group relative to CRS and control. Inset images in the top row represent negative control slides.

FIGS. 3A-B are a set of high magnification histologic images (bar=50 μm) of P-gp immunostaining in CRSwNP (A) and Control (B) subjects with matched propidium iodide nuclear stains (lower panel). Note the circumferential membranous P-gp expression subtending both the apical and basolateral surfaces of the epithelial cells.

Note the significant reduction in LPS stimulated TSLP secretion following inhibition of P-gp with PSC 833.

Figure 11:
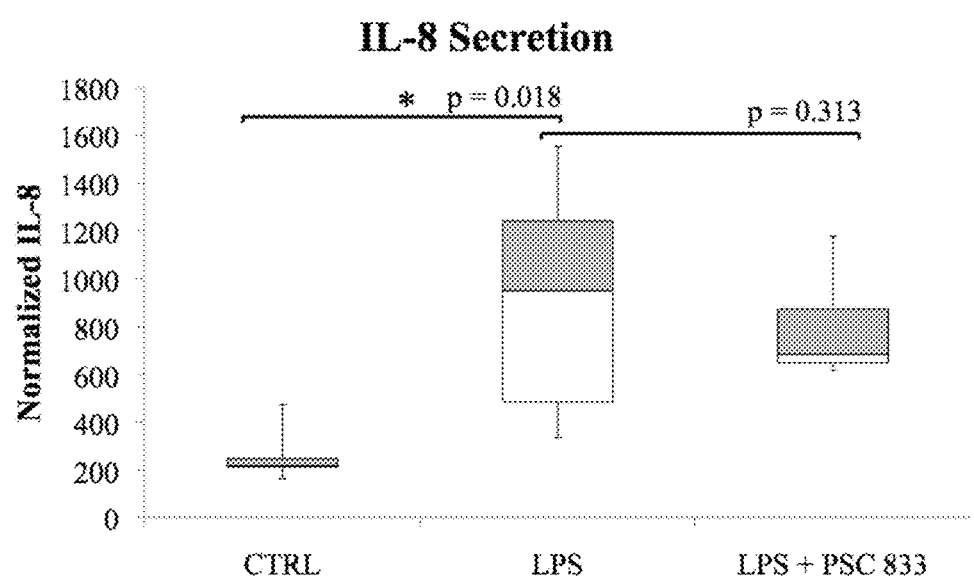

FIG. 11 is a box graph showing secreted IL-8 concentration (normalized to total media protein) in the control condition (CTRL) following exposure to culture media alone as compared to PNECCs exposed to media+LPS (0.05 mg/mL), and media+LPS (0.05 mg/mL)+PSC 833 (8micM). In this case PSC 833 failed to significantly impair IL-8 secretion suggesting that P-gp mediated secretion is selective to specific cytokines.

Figure 12:
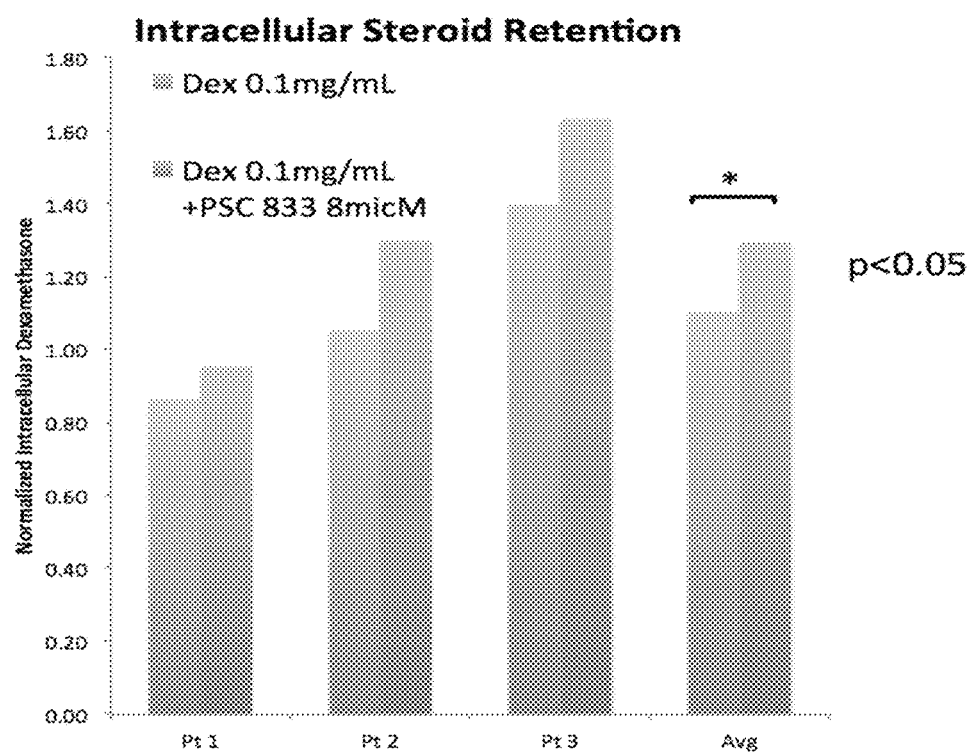

FIG. 12 is a bar graph showing that treatment with the P-gp inhibitor PSC 833 resulted in increased intracellular dexamethasone retention in primary sinonasal epithelial cells relative to uninhibited cells.

FIG. 13A is a bar graph showing that treatment with the P-gp inhibitor Verapamil or Zosuquidar resulted in increased intracellular prednisone retention in primary sinonasal epithelial cells relative to uninhibited cells. FIG. 13B is a bar graph showing that treatment with the P-gp inhibitor Verapamil or Zosuquidar resulted in increased intracellular dexamethasone retention in primary sinonasal epithelial cells relative to uninhibited cells.

Figure 14:
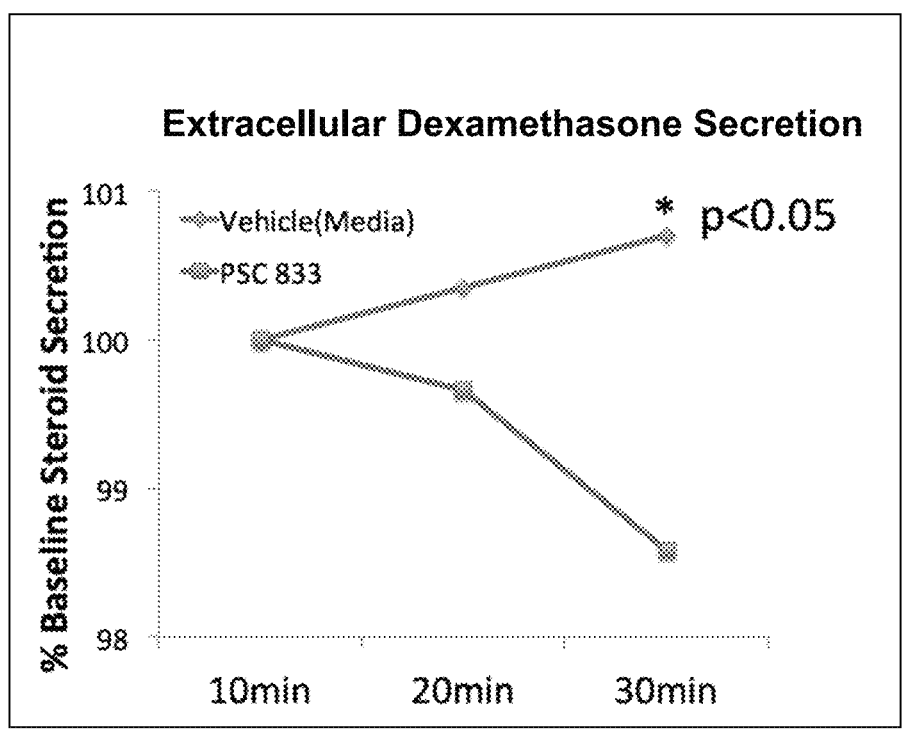

FIG. 14 is a line graph showing that treatment with the P-gp inhibitor PSC 833 resulted in increased intracellular dexamethasone retention in nasal polyp explants relative to uninhibited polyp explants.

Figure 15:
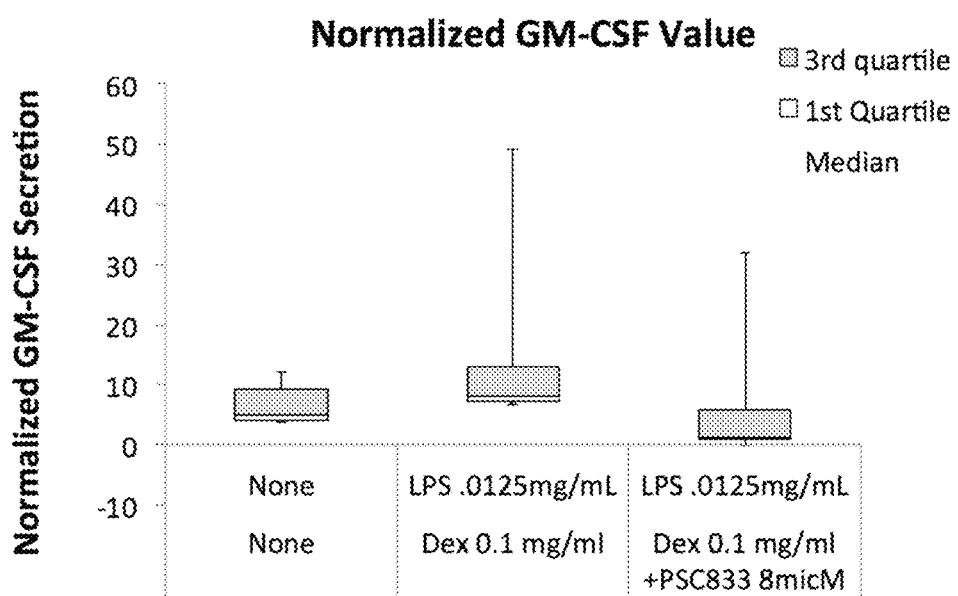

FIG. 15 is a box graph showing that GM-CSF secretion is reduced in LPS-stimulated cells treated with both dexamethasone and PSC833 as compared to dexamethasone treatment alone.

Figures 16A, 16B:
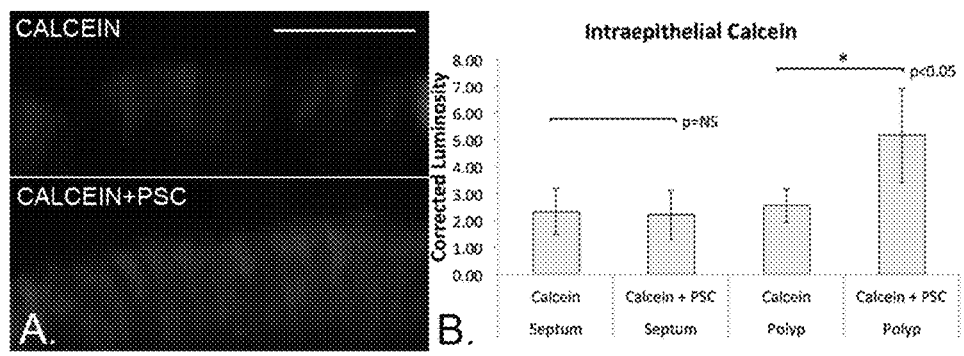

FIG. 16A is a set of fluorescent images of epithelial calcein staining in nasal polyp explants with or without the presence of PSC 833(bar=50 μm). FIG. 16B is a bar graph demonstrating the corrected luminosity of both septal and nasal polyps explants with or without the presence of PSC 833(n=4, each). The increase in calcein luminosity following PSC 833 mediated inhibition is proportionate to the degree of P-gp activity.

Figure 17A:
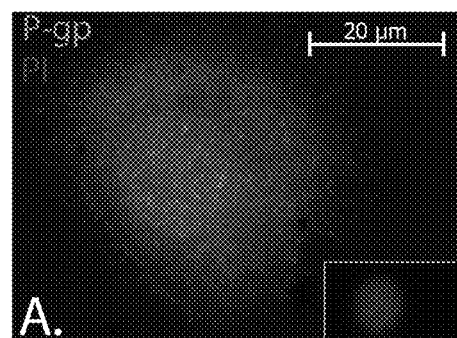
Figure 17B:
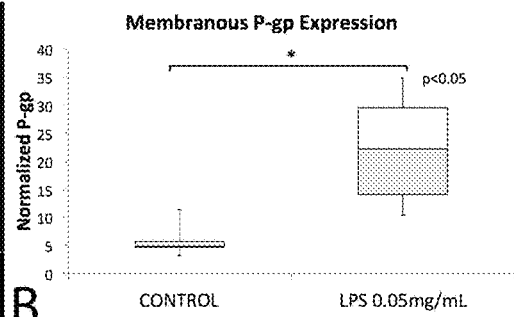

FIG. 17A is a FIHC image demonstrating pattern of P-gp expression in submerged CRSwNP HSNECC with propidium iodide (PI) nuclear counterstain. Inset represents control slide with primary antibody omitted. FIG. 17B is a box and whisker plot of membranous P-gp expression (ng/mL) normalized to total cytoplasmic protein (mcg/mL) demonstrating a significant upregulation following LPS exposure as compared to cells exposed to media alone.

Figure 18:
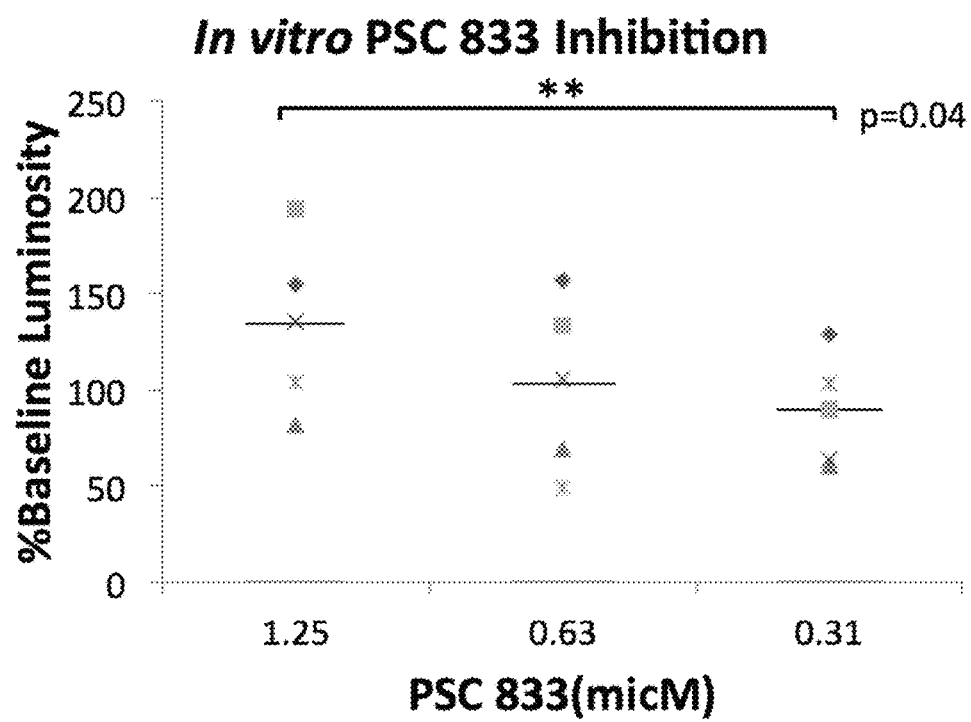

FIG. 18 is a dot plot demonstrating a significant dose-dependent inhibition of P-glycoprotein following PSC 833 exposure. The increase in mean calcein fluorescence following exposure to varying concentrations of PSC 833 relative to uninhibited control cells is proportionate to a successive reduction in P-gp activity.

FIGS. 19A and 19B are box and whisker plots of cytokine secretion of GM-CSF (A) and IL-6 (B) under control, LPS stimulated, and LPS stimulated+P-gp inhibitor conditions (n=5, each). The y-axis represents secreted cytokine concentration (pcg/mL) normalized to total media protein (mcg/mL)×100. FIGS. 19C and 19D are scatter plots showing the positive correlation between LPS stimulated normalized GM-CSF (C) and IL-6 (D) secretion and membranous P-gp expression.

Figure 20A:
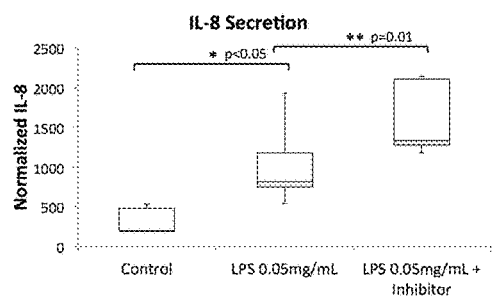
Figure 20B:
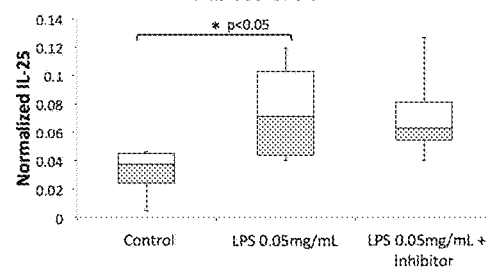
Figure 20C:
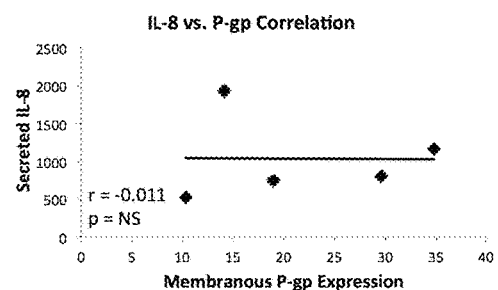
Figure 20D:
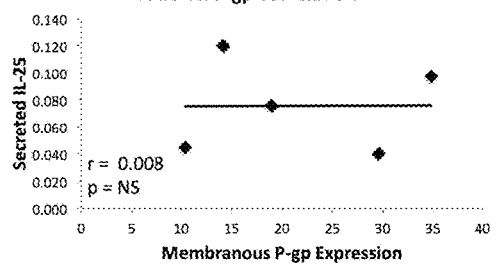

FIGS. 20A and 20B are box and whisker plots of cytokine secretion of IL-8 and IL-25 under control, LPS stimulated, and LPS stimulated+P-gp inhibitor conditions. The y-axis represents secreted cytokine concentration (pcg/mL) normalized to total media protein (mcg/mL)×100. FIGS. 20C and 20D are scatter plots showing the lack of correlation between LPS stimulated normalized IL-8 (C) and IL-25 (D) secretion and membranous P-gp expression.

Figure 21A:
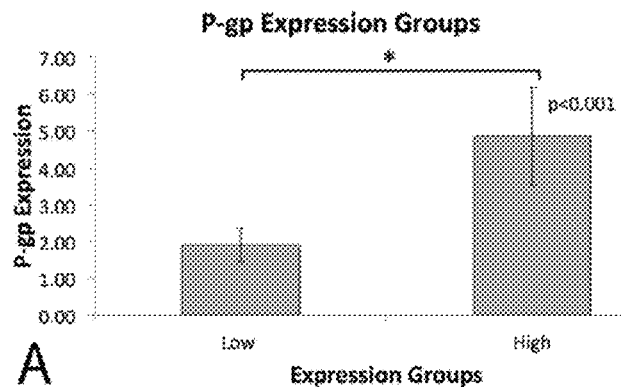
Figure 21B:
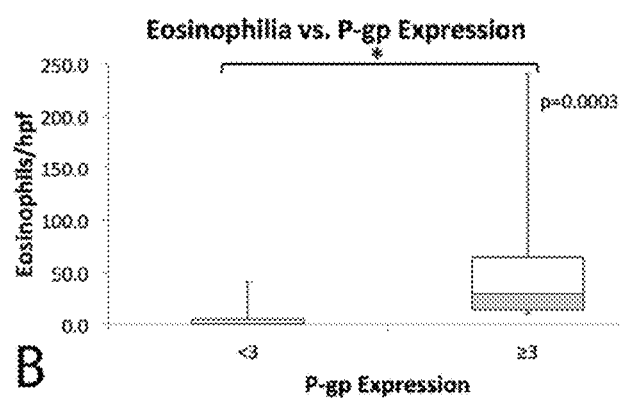
Figure 21C:
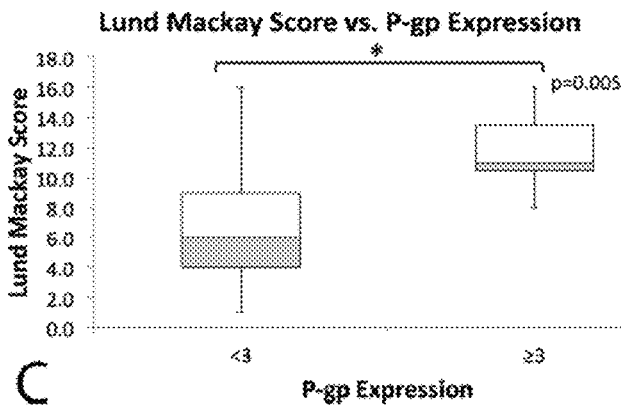

FIG. 21A is a bar graph demonstrating the mean P-gp epithelial/background staining ratios between the low and high P-gp expressing patient groups. FIG. 21B is a box and whisker plot demonstrating the distribution of eosinophils/hpf between the low and high P-gp expressing patient groups. FIG. 21C is a box and whisker plot demonstrating the distribution of Lund-Mackay scores between the low and high P-gp expressing patient groups.

Figures 22A, 22B, 22C, 22D, 22E, 22F:
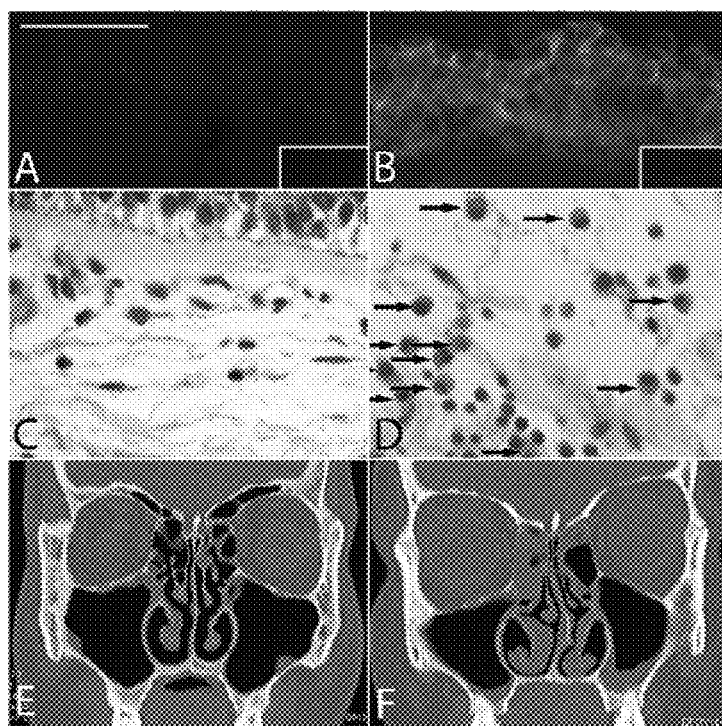

FIGS. 22A and B are fluorescent immunohistochemical images of mucosa depicting representative (A) low epithelial P-gp expression and (B) high epithelial P-gp expression (bar=50 μM, lower right inset represents negative control in which the primary antibody was omitted). FIGS. 22C and D are matched high powered (400×) H&E stromal images depicting the absence (C) and presence (D) of mucosal eosinophilia (black arrows denote individual eosinophils). Note the thickened basement membrane in C is consistent with CRSsNP. FIGS. 22E and F are coronal CT scans demonstrating increased radiographic inflammation in the patient with high P-gp expression (F) relative to the patient with low P-gp expression (E).

FIG. 23A is a bar graph demonstrating the mean P-gp epithelial/background staining ratios between the low and high P-gp-expressing patient groups. FIG. 23B is a box and whisker plot demonstrating the distribution of serum eosinophil between the low and high P-gp-expressing patient groups.

Figure 24A:
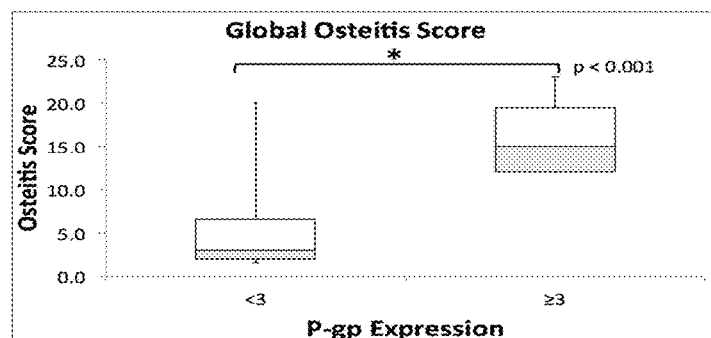
Figure 24B:
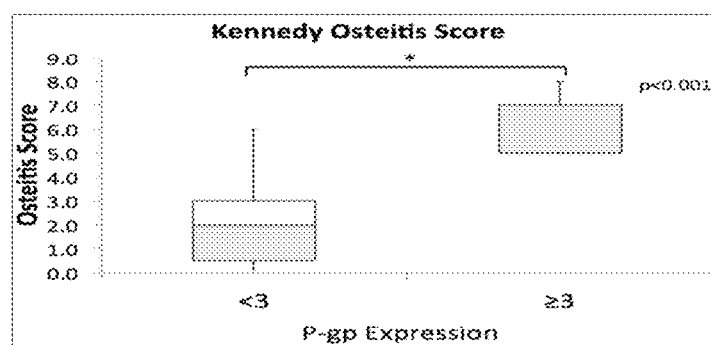
Figure 24C:
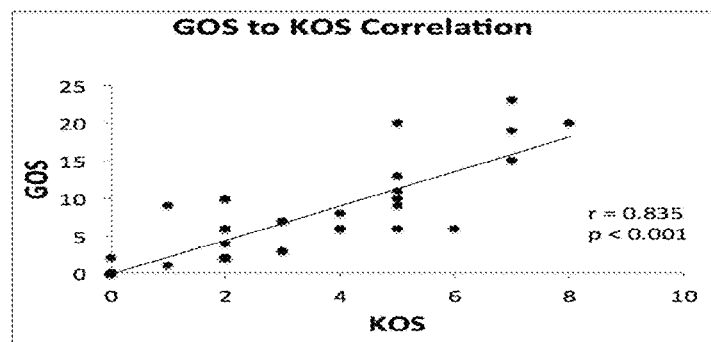

FIG. 24A is a box and whisker plot demonstrating the distribution of GOS between the low and high P-gp-expressing patient groups. FIG. 24B is a box and whisker plot demonstrating the distribution of KOS between the low and high P-gp expressing patient groups. FIG. 24C is a scatter plot of both osteitis scoring systems demonstrating a significant, high correlation between KOS and GOS.

DETAILED DESCRIPTION

About 16% of the adult population in the United States suffers chronic rhinosinusitis (Blackwell et al., Vital Health Stat. 10. 2002 May; (205):1-109). According to U.S. Centers for Disease Control and Prevention, over 30 million Americans have sinusitis, resulting in about 200,000 to 500,000 sinus surgeries and 23 million missed work days per year.

The primary objectives for treating rhinosinusitis are reduction of inflammation, eradication of infection, draining of the sinuses, and ensuring that the paranasal sinuses are and remain open.

Described herein are methods for treating rhinosinusitis in subjects with P-glycoprotein (P-gp) inhibitors. P-glycoprotein (P-gp) is an ATP dependent efflux pump. The data shown herein demonstrate that P-gp is overexpressed in subjects with rhinosinusitis, and P-gp functions as an immunomodulator through regulation of epithelial cytokine secretion. Therefore, P-gp contributes to the etiopathogenesis of sinonasal inflammation, and P-gp inhibitors can be used for treating subjects with rhinosinusitis. P-gp inhibitors can also be used in combination with other conventional treatments, e.g., drugs such as corticosteroids and/or antibiotics, to potentiate the effect of treatment by enhancing intracellular retention. For example, P-gp inhibitors can be used in combination with a corticosteroid, e.g., selected from dexamethasone, prednisolone, triamcinolone, cortisol, prednisone, budesonide, mometasone, fluticasone, flunisolide, and betamethasone. In some embodiments, P-gp inhibitors are used in combination with an antibiotic, e.g., selected from macrolides, e.g., erythromycin; penicillins, e.g., amoxicillin, beta-lactam, ampicillin; tetracyclines, e.g., doxycycline, tetracycline; sulfonamides, e.g. mafenide, sulfacetamide; fluoroquinolones; and cephalosporins, e.g., ceftaroline fosamil, ceftobiprole. In some embodiments, P-gp inhibitors are used in combination with a corticosteroid and an antibiotic.

Conventional Treatment of Rhinosinusitis

The present methods can be used in combination with present conventional treatments of rhinosinusitis, e.g., as follows. Most subjects with rhinosinusitis caused by bacteria are treated with antibiotics along with a nasal decongestant. The most common side effect for nearly all antibiotics is gastrointestinal distress. Certain drugs, including some over-the-counter medications, interact with antibiotics, and all antibiotics carry the risk for allergic reactions, which can be serious in some cases. Failure to take all prescribed antibiotics may increase the risk for reinfection and also for development of antibiotic-resistant bacteria. The usefulness of antibiotics in treating chronic sinusitis is highly debated, as some symptoms persist even after prolonged courses of antibiotics. Furthermore, a vast majority of sinusitis is caused by viruses and will not respond to antibiotic treatment.

Nasal decongestants may dry out the affected areas and damage tissues. With prolonged use, nasal decongestants become ineffective, and the tendency is to increase the frequency of use. Withdrawal from over-frequent decongestant use can itself cause symptoms of rhinosinusitis and the return of nasal congestion, a phenomenon known as the "rebound effect." Short-acting nasal decongestants may cause rebound effect after only eight hours. Eventually, the inflammation can become worse than before the decongestant was taken. Thus, nasal decongestants are generally recommended for no more than one to three days of use because of this risk.

Steroid nasal sprays are commonly used to treat inflammation in chronic sinusitis. For subjects with severe chronic sinusitis, doctors may prescribe oral steroids, such as prednisone. Since oral steroids have serious side effects, they are prescribed only when other medications have not been effective.

When medications fail, surgery may be the only alternative in treating chronic sinusitis. Presently, the most commonly done surgery is functional endoscopic sinus surgery, in which the sinuses are reached through the nasal passage via endoscopy, and the diseased and thickened tissues from the sinuses are removed to enlarge the sinus passageway to the nostril and allow for drainage and improved topical drug delivery. This type of surgery is less invasive than traditional open sinus surgery techniques. Symptoms of chronic sinusitis sometimes persist after surgery, however, because of continued inflammation, growth of new nasal polyps, or scarring from the procedure.

P-Glycoprotein

P-glycoprotein is a 170-kDa glycoprotein encoded by the MDR1 (ABCB1) gene located on chromosome 7q21.12 and was first identified in the CHO cell line (Fernandez et al., J Pharm. Pharm. Sci. 2004 Nov. 17; 7(3):359-71). P-gp is a member of the ATP-binding cassette (ABC) transporter family and is capable of energy dependent transport of a variety of intracellular substrates (Golden et al., J Pharm Sci. 2003; 92(9):1739-53). P-gp is located within the plasma membrane and functions to extrude xenobiotic agents against their concentration gradient (Ehrhardt et al., Pharm. Res. 2003 April; 20(4):545-51). Substrate recognition of P-gp occurs by a variety of mechanisms including the presence of electron donor groups which bind putative reactive hydrogen bonding sites in the interior channels formed by the 12 transmembrane helices (Golden et al., 2003).

P-gp is constitutively expressed on multiple cell types including the apical membrane of intestinal mucosal cells, the brush border of renal proximal tubules, the blood-brain barrier, and lower airway epithelial cells (Bleier B S, Int. Forum Allergy Rhinol. 2012; 2:122-125). Due to the selective distribution at the port of drug entry and exit, P-gp functions as a biochemical barrier for entry of xenobiotics and as a vacuum cleaner to expel them from the organs, such as brain, liver, kidney, and ultimately from systemic circulation (Varma et al., Pharmacological Research 2003; 48: 347-359). This xenobiotic excretion function belies the role of P-gp in reducing the systemic bioavailability of a variety of drugs. Through increased expression and active drug efflux in malignancy, P-gp has also been shown to confer chemotherapeutic resistance (Fernandez et al., 2004).

While the efflux behavior of P-gp is well established, the potential for the role of P-gp as an immunomodulator is a new concept. In a P-gp knockout mouse (Mdr1a/1b$^{-/-}$), there was diminished dendritic cell (DC) maturation and subsequent DC induced T-cell response which correlated with decreased Th1 and Th2 cytokine levels (Kooij et al., PLoS One. 2009 Dec. 8; 4(12):e8212). In the lower airway, inhalational steroid exposure has been shown to decrease the expression of lymphocyte P-gp (Kopriva et al., J Asthma. 2009 May; 46(4):366-70).

P-Glycoprotein Inhibitors

A number of inhibitors of P-gp are known in the art (Varma et al., 2003). In general, P-gp can be inhibited (1) by blocking its substrate binding site; (2) by interfering with its ATPase activity (Shapiro, et al., Biochem Pharmacol 1997; 53:587-96); or (3) by decreasing its expression level either transcriptionally or posttranscriptionally. (Drori et al., Eur J Biochem 1995; 228:1020-9).

Based on specificity and affinity, P-gp inhibitors are classified into three generations. First-generation P-gp inhibitors are known pharmacological compounds that are in clinical use, or were developed for, for other indications but have been shown to inhibit P-gp. These include calcium channel blockers such as verapamil; immunosuppressants like cyclosporin A; anti-hypertensives, reserpine, quinidine and yohimbine; and anti-estrogens like tamoxifen and toremifena (Varma et al., 2003). The usage of these compounds has been limited by their toxicity due to the high serum concentrations achieved with the dose that is required to inhibit P-gp when administered systemically.

Second-generation P-gp modulators are agents that lack the pharmacological activity of the first-generation compounds and usually possess a higher P-gp affinity. Second-generation P-gp inhibitors include the non-immunosuppresive analogues of cyclosporin A such as PSC 833 (Valspodar: 6-[(2S,4R,6E)-4-methyl-2-(methylamino)-3-oxo-6-octenoic acid]-7-L-valine-cyclosporin A); verapamil isomers such as D-isomer of verapamil, R-verapamil, and dexverapamil; and other inhibitors such as VX-710 (Biricodar: 1,7-di(pyridin-3-yl)heptan-4-yl (2S)-1-[oxo(3,4,5-trimethoxyphenyl)acetyl]piperidine-2-carboxylate); GF120918 (Elacridar: N-(4-(2-(6,7-dimethoxy-3,4-dihydroisoquinolin-2(1H)-yl)ethyl)phenyl)-5-methoxy-9-oxo-9,10-dihydroacridine-4-carboxamide hydrochloride); and MS-209 (Dofequidar fumarate: 1-(4-(2-hydroxy-3-(quinolin-5-yloxy)propyl)piperazin-1-yl)-2,2-diphenylethanone)

(Varma et al., 2003). However, this class of compounds often inhibits two or more ABC transporters, leading to some drug-drug interactions.

The third-generation P-gp blockers are under development with the primary purpose to improve the treatment of multidrug resistant tumors and to inhibit P-gp with high specificity and toxicity. Examples of the third-generation P-gp inhibitors include LY335979 (Zosuquidar: (2R)-1-{4-[(1aR,6r,10bS)-1,1-Difluoro-1,1a,6,10b-tetrahydrodibenzo[a,e]cyclopropa[c]cyclohepten-6-yl]piperazin-1-yl}-3-(quinolin-5-yloxy)propan-2-ol,trihydrochloride); OC144093 (4-[2-[4-[(E)-3-ethoxyprop-1-enyl]phenyl]-4-[4-(propan-2-ylamino)phenyl]-1H-imidazol-5-yl]-N-propan-2-ylaniline); R-101933 (Laniquidar: methyl 11-(1-(4-(quinolin-2-ylmethoxy)phenethyl)piperidin-4-ylidene)-6,11-dihydro-5H-benzo[d]imidazo[1,2-a]azepine-3-carboxylate); XR9576 (Tariquidar: N-[2-[[4-[2-(6,7-Dimethoxy-3,4-dihydro-1H-isoquinolin-2-yl)ethyl]phenyl]carbamoyl]-4,5-dimethoxyphenyl]quinoline-3-carboxamide); XR9051 (3-((Z)—((Z)-5-benzylidene-4-methyl-3,6-dioxopiperazin-2-ylidene)methyl)-N-(4-(2-(6,7-dimethoxy-3,4-dihydroisoquinolin-2(1H)-yl)ethyl)phenyl)benzamide). Some third-generation P-gp modulators such as LY335979, OC144093, and XR9576 are shown to be highly potent and selective inhibitors of P-gp with a potency of about 10-fold more than the first and second-generation inhibitors. (Varma et al., 2003).

Treatment of Rhinosinusitis Using P-Glycoprotein Inhibitors

While the expression of P-gp has been studied in the lower airway, very little is known with respect to its presence in the upper airway or its relationship to chronic sinonasal inflammation. Furthermore, there is no report on the expression of P-gp across disease states or between sinus and adjacent intranasal sub sites. Therefore, the pattern and degree of epithelial P-gp expression was examined in subjects having chronic sinusitis (CRS) with or without nasal polyposis (NP) and in control subjects.

The data presented herein show that the expression of P-gp is negligible in healthy sinus mucosa, but is significantly elevated in the epithelial layer of sinus mucosa in subjects having CRS with or without NP relative to other non-diseased sinonasal subsites.

The sinonasal epithelium functions as a barrier organ against the external environment and is endowed with an array of innate and adaptive immunologic mechanisms to combat extrinsic pathogens. It has been suggested that sinonasal epithelial cells may function as primary actors in the initiation and maintenance of chronic sinonasal inflammation through the elaboration of an array of cytokines and subsequent recruitment of professional immune cells (Reh et al., Am. J Rhinol. Allergy. 2010; 24(2):105-9). While these studies suggest that epithelial cells are capable of orchestrating an innate immune response, the post-translational mechanisms governing non-canonical cytokine secretion at the cellular level are not fully understood.

The data presented herein show that membrane bound P-gp is present and functionally active in primary nasal epithelial cells, and P-gp inhibitor (e.g., PSC 833) exposure results in a significant reduction in stimulated cytokine secretion of those primary nasal epithelial cells. As demonstrated herein, P-gp participates in modulating cytokine secretion and inflammation at the nasal mucosal surface. Furthermore, P-gp inhibition in epithelial cells is shown to result in increased intracellular steroid retention and potentiate the anti-inflammatory effect of steroid.

Collectively, the present data show that P-gp is overexpressed in sinus mucosa of subjects having rhinosinusitis, and P-gp functions as an immunomodulator through regulation of epithelial cytokine secretion. Therefore, P-gp contributes to the etiopathogenesis of sinonasal inflammation and P-gp inhibitors are promising novel medicines for treating rhinosinusitis in order to reduce the cytokine secretion which leads to the development of sinonasal inflammation.

In some embodiments, a subject having rhinosinusitis is identified and treated by administering to the subject an effective amount of a P-gp inhibitor. The subject having rhinosinusitis may be identified by one of skill in the art based on known methods, e.g., based on detection of the presence of symptoms, by endoscopy, or by computed tomography. The efficacy of the treatment may be monitored by methods known in the art, e.g., by monitoring symptoms, by endoscopy or computed tomography. Improvements of the subject include a better symptom score, e.g. a better SNOT-22 or VAS score; a reduction in inflammation or nasal polyp burden as revealed by endoscopy, e.g. a better Lund-Kennedy score; or a reduction in mucosal thickening or sinus opacification as revealed by computed tomography (CT), e.g. a better Lund-Mackay score. The 22-item Sinonasal Outcomes Test (SNOT-22) is a questionnaire encompassing 22 major symptoms on rhinosinusitis and nasal polyps, and serves as a valuable tool to measure the severity of a subject's symptoms and their impact on health-related quality of life (Quintanilla-Dieck, et al., International Forum of Allergy & Rhinology 2012; 2(6):437-443). The SNOT-22 assessed 12 nasal- and sinus-related symptoms (nasal blockage, loss of sense of taste and smell; need to blow nose, sneezing, runny nose, cough, postnasal discharge, thick nasal discharge, ear fullness, dizziness, ear pain, and facial pain/pressure) and 10 psychological and behavioral symptoms (difficulty falling asleep, waking up at night, lack of a good night's sleep, waking up tired, fatigue, reduced productivity, reduced concentration, frustrated/restless/irritable, sad, and embarrassed) with participants scoring each symptom on a scale of 0 (absent) to 5 (severe) on average for the last week, for a total score range of 0 to 100. The SNOT-22 score is the mean for the 22 scores (Piccirillo et al., Otolaryngol Head Neck Surg 2002; 126:41-47). The 10-symptom visual analog (VAS) scale is a questionnaire based on the major and minor symptom diagnostic criteria for CRS as described by the American Academy of Otolaryngology—Head and Neck Surgery TFR. The VAS assessed subject-reported severity of each of the following symptoms on average experienced during the prior week: nasal drainage of pus, nasal obstruction/congestion, impaired sense of smell, facial pressure/pain, headache, bad breath, weakness/fatigue, dental pain, ear fullness/pain, and cough (Ryan, et al., Laryngoscope 2011; 121:674-678). The Lund-Kennedy endoscopy scoring system quantifies the pathologic states of the nose and paranasal sinuses as assessed by nasal endoscopy, focusing on the presence of polyps, discharge, edema, scarring or adhesions, and crusting (Ryan, et al., 2011). The Lund Mackay CT scoring system is the most widely used CT grading system for chronic rhinosinusitis. This scoring system consists of a scale of 0-2 dependent on the absence (0), partial (1) or complete (2) opacification of the sinus system and the osteomeatal complex as assessed by CT imaging (Hopkins et al., Otolaryngology—Head and Neck Surgery 2007; 137:555-561).

In some embodiments, a subject with rhinosinusitis is treated with a P-gp inhibitor in an amount sufficient to inhibit P-gp function. The P-gp inhibitor could be a first generation compound, e.g. a calcium channel blocker such as verapamil, an immunosuppressant like cyclosporin A, an anti-hypertensive, a reserpine, a quinidine or yohimbine, or an anti-estrogen like tamoxifen or toremifena. Preferably, the P-gp inhibitor is a second or third generation compound, e.g. PSC 833, D-isomer of verapamil, dexverapamil, VX-710, GF120918, MS-209, R101933, LY335979, OC144093, XR9051, or XR9576.

In other embodiments, a subject with rhinosinusitis is treated with a P-gp inhibitor in an amount sufficient to decrease P-gp expression in the subject's sinonasal epithelial cells, either transcriptionally or posttranscriptionally.

In some embodiments, the P-gp inhibitor is administered systemically, e.g., orally, intravenously, intradermally, or subcutaneously. In other embodiments, the P-gp inhibitor is administered locally to the subject's nasal passage and sinuses by an inhalation device, by flushing, or by spraying. In some embodiments, a subject with rhinosinusitis is treated with nasal drops or sprays comprising an effective amount of a P-gp inhibitor. An effective amount of the P-gp inhibitor can be delivered to the subject's nasal passage and sinuses in a liquid form by flushing or spraying. An effective amount of a P-gp inhibitor can also be delivered to the nasal passage and sinuses of a subject with rhinosinusitis in an aerosolized form by an inhalation device, such as a nebulizer, an inhaler, or an OptiNose.

In some embodiments, a subject with rhinosinusitis is treated with a P-gp inhibitor in combination with other conventional treatments, e.g., drugs such as corticosteroids and/or antibiotics, to potentiate the effect of treatment. For example, P-gp inhibitors may be used in combination with a corticosteroid selected from dexamethasone, prednisolone, triamcinolone, cortisol, prednisone, budesonide, mometasone, fluticasone, flunisolide, and betamethasone. In some embodiments, P-gp inhibitors are used in combination with an antibiotic selected from macrolides, e.g., erythromycin; penicillins, e.g., amoxicillin, beta-lactam, ampicillin; tetracyclines, e.g., doxycycline, tetracycline; sulfonamides, e.g. mafenide, sulfacetamide; fluoroquinolones; and cephalosporins, e.g., ceftaroline fosamil, ceftobiprole. In some embodiments, P-gp inhibitors are used in combination with a corticosteroid and an antibiotic.

In some embodiments, when a subject with rhinosinusitis has nasal polyps, surgical removal of such nasal polyps can be performed in addition to administration of a P-gp inhibitor to the subject. Thus, a subject with rhinosinusitis may undergo both surgery and treatment with a P-gp inhibitor.

In some embodiments, a subject continues to experience symptoms of chronic sinusitis after a sinus surgery, and a P-gp inhibitor-eluting implant, stent, or spacer is used to maintain sinus patency in the subject. During the sinus surgery, a P-gp inhibitor eluting device is implanted, e.g., in the ostia of the paranasal sinuses to prop open the ostia while locally eluting a P-gp inhibitor to reduce inflammation of the sinonasal epithelium after the surgery. The P-gp inhibitor eluting device can be made from bioabsorbable material so that the implant will be absorbed within a short period of time after the implantation and no surgical removal of the implant is necessary. The P-gp inhibitor eluting device can be in the form of solid, semisolid, gel, polymer, or particle. In some embodiments, the P-gp inhibitor eluting device is a bioabsorbable gel such as an alginate gel (e.g., sodium alginate), a cellulose-based gel (e.g., carboxymethyl cellulose or carboxyethyl cellulose), or a chitosan-based gel (e.g., chitosan glycerophosphate; see, e.g., Bleier et al., Am J Rhinol Allergy 23, 76-79, 2009).

In some embodiments, a tissue sample, e.g., a sinus mucosal biopsy sample, can be obtained from a subject having rhinosinusitis and one or more tests can be performed on these biopsy samples to assist in selecting a therapy for the subject. For example, levels of P-gp expression in the nasal epithelium can be determined using methods known in the art, e.g., quantitative fluorescent immunohistochemistry. When a P-gp expression level in the nasal epithelium is determined to be above a threshold (i.e., a reference level), a therapy comprising a P-gp inhibitor as described herein can be selected to treat rhinosinusitis in the subject.

In some embodiments, sinus mucosal biopsy samples from a subject having rhinosinusitis and the average number of eosinophils per high powered field can be calculated, e.g., using light microscopy and staining with hematoxylin and eosin. As demonstrated herein, P-gp expression levels correlate with tissue eosinophilia, thus high levels of tissue eosinpophelia (i.e., levels above a reference level) can be used as a proxy for high levels of P-Gp expression. A therapy as described herein comprising administration of a P-gp inhibitor can be selected to treat rhinosinusitis in the subject when the average number of eosinophils per high powered field is determined to be above a threshold (i.e., reference level).

In some embodiments, computed tomography (CT) can be performed to score osteitis in a subject having rhinosinusitis. For example, a Kennedy Osteitis Score (KOS) (Lee J T, Kennedy D W, Palmer J N, Am J Rhinol 20:278-282, 2006) or Global Osteitis Score (GOS) (Georgalas C, Videler W, Freling N, Clin Otolaryngol 35:455-461, 2010) can be determined for the bony walls of the paranasal sinuses as previously described. As demonstrated herein, these osteitis scores correlate with P-gp expression level in patients having chronic sinusitis, and thus a high osteitis score can be used as a proxy for high P-gp expression levels. When an osteitis score is determined to be above a threshold (i.e., a reference level), a therapy as described herein comprising administration of a P-gp inhibitor can be selected to treat rhinosinusitis in the subject.

One of skill in the art would readily be able to determine and select a suitable reference level. For example, a reference level can be determined as a median, average, or cutoff point for a percentile of the population (e.g., the cutoff for the top half, top tertile, top quartile, top quintile, and so on). A reference level can be selected that represents a level of P-gp expression, eosinophilia, KOS, or GOS in a subject that would be likely to benefit from treatment with a P-gp inhibitor, and levels at or above that reference level indicate that the subject should be treated with a method comprising administration of a P-gp inhibitor as described herein.

Methods for Selecting a Subject for Participation, or Stratifying Subjects, in a Clinical Study Also provided are methods of selecting a subject for participation in, or stratifying subjects in, a clinical study of a treatment for rhinosinusitis. Such methods can include determining a level of epithelial P-gp expression in a sinus mucosal biopsy sample from a subject, comparing the P-gp level in the sample to a reference P-gp level, and selecting for participation a subject having an elevated P-gp level in the sample compared to the reference P-gp level in a clinical trial of a treatment for rhinosinusitis, or stratifying subjects in a clinical trial based on P-gp levels. In some embodiments, a subject can be excluded from participation in a clinical study of a treatment for rhinosinusitis if the subject has no significant change or a decrease in the P-gp level in the sample compared to the reference P-gp level.

Also provided are methods of selecting a subject for participation in, or stratifying subjects in, a clinical study for a treatment for rhinosinusitis. Such methods include determining a P-gp level in a first biopsy sample obtained from a subject at a first time point, determining a P-gp level in a second biopsy sample obtained from the subject at a second time point, comparing the P-gp level in the first biopsy sample to the P-gp level in the second biopsy sample, and selecting a subject having an elevated P-gp level in the second biopsy sample compared to the P-gp level in the first biopsy sample for participation in a clinical trial of a treatment for rhinosinusitis, or stratifying subjects in a clinical trial based on changing P-gp levels. In some embodiments, a subject can be excluded from participation in a clinical study of a treatment for rhinosinusitis if the subject has no significant change or a decrease in the P-gp level determined at the second time point compared to the P-gp level determined at the first time point. In some embodiments, the treatment for rhinosinusitis is a pharmacological treatment (e.g., administration of one or more pharmaceutical agents) or the implantation of an eluting implant, stent, or spacer.

In some embodiments, additional clinical scores can be used to assist in selecting a subject for participation in, or stratifying subjects in, a clinical study of a treatment for rhinosinusitis. For example, sinus mucosal biopsy samples can be processed for hematoxylin and eosin staining and the average number of eosinophils per high powered field can be calculated and used in selecting a subject for participation in, or stratifying subjects in a clinical study of a treatment for rhinosinusitis. For example, subjects with levels of eosinophilia above a reference level can indicate that the subject should be selected or stratified.

In some embodiments, computed tomography (CT) can be performed to score osteitis in a subject having rhinosinusitis. The osteitis score, e.g., Kennedy Osteitis Score (KOS) or Global Osteitis Score (GOS) can be used in selecting a subject for participation in, or stratifying subjects in, a clinical study of a treatment for rhinosinusitis. For example, subjects with GOS or KOS above a reference level can indicate that the subject should be selected or stratified.

The clinical studies may be performed by a health care professional (e.g., a physician, a physician's assistant, a nurse, a phlebotomist, or a laboratory technician) in a health care facility (e.g., a hospital, a clinic, or a research center). The biopsy samples may be obtained from subjects that present with one or more (e.g., at least two, three, four, or five) symptoms of rhinosinusitis.

Pharmaceutical Compositions, Dosage, and Methods of Administration

The methods of treatment described herein also include the use of pharmaceutical compositions, which include P-gp inhibitors described herein as active ingredients. In some embodiments the composition also includes one or more supplementary active compounds incorporated therein, e.g., one or more corticosteroids and/or one or more antibiotics. The corticosteroid can be, e.g., selected from dexamethasone, prednisone, prednisolone, triamcinolone, cortisol, budesonide, mometasone, fluticasone, flunisolide, or betamethasone. The antibiotic can be, e.g., selected from erythromycin, doxycycline, tetracycline, penicillin, beta-lactam, macrolide, fluoroquinolone, cephalosporin, and sulfonamide. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders, for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the therapeutic compounds are prepared with carriers that will protect the therapeutic compounds against rapid elimination from the body, such as a controlled release formulation, including implants and microencapsulated delivery systems.

The pharmaceutical compositions can be included in a container, pack, or dispenser together with instructions for administration.

In some embodiments, a kit for treating rhinosinusitis in a subject is provided. Such a kit comprises a pharmaceutical composition comprising an effective amount of a P-glycoprotein inhibitor, optionally a corticosteroid and/or an antibiotic, and a device for delivering the pharmaceutical composition to the subject's nasal passage and sinuses, such as a nebulizer, an inhaler, or an OptiNose. The device may deliver the pharmaceutical composition to the subject's nasal passage and sinuses in a liquid or an aerosolized form.

In non-limiting examples, the pharmaceutical composition containing at least one pharmaceutical agent is formulated as a liquid (e.g., a thermosetting liquid), as a component of a solid (e.g., a powder or a biodegradable biocompatible polymer (e.g., a cationic biodegradable biocompatible polymer)), or as a component of a gel (e.g., a biodegradable biocompatible polymer). In some embodiments, the at least composition containing at least one pharmaceutical agent is formulated as a gel selected from the group of an alginate gel (e.g., sodium alginate), a cellulose-based gel (e.g., carboxymethyl cellulose or carboxyethyl cellulose), or a chitosan-based gel (e.g., chitosan glycerophosphate). Additional, non-limiting examples of drug-eluting polymers that can be used to formulate any of the pharmaceutical compositions described herein include, carrageenan, carboxymethylcellulose, hydroxypropylcellulose, dextran in combination with polyvinyl alcohol, dextran in combination with polyacrylic acid, polygalacturonic acid, galacturonic polysaccharide, polysalactic acid, polyglycolic acid, tamarind gum, xanthum gum, cellulose gum, guar gum (carboxymethyl guar), pectin, polyacrylic acid, polymethacrylic acid, N-isopropylpolyacrylomide, polyoxyethylene, polyoxypropylene, pluronic acid, polylactic acid, cyclodextrin, cycloamylose, resilin, polybutadiene, N-(2-Hydroxypropyl)methacrylamide (HPMA) copolymer, maleic anhydrate-alkyl vinyl ether, polydepsipeptide, polyhydroxybutyrate, polycaprolactone, polydioxanone, polyethylene glycol, polyorganophosphazene, polyortho ester, polyvinylpyrrolidone, polylactic-co-glycolic acid (PLGA), polyanhydrides, polysilamine, poly N-vinyl caprolactam, and gellan.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

EXAMPLES

The invention is further described in the following examples, which do not limit the scope of the invention described in the claims.

Example 1

MDR1/P-Gp is Overexpressed in the Epithelial Layer of Sinus Mucosa in Subjects Having Chronic Rhinosinusitis with or without Nasal Polyposis Relative to Control Subjects and Non-Diseased Adjacent Intranasal Subsites While the expression of P-gp has been studied in the lower airway, very little is known with respect to its presence in the upper airway or its relationship to chronic sinonasal inflammation. Furthermore, there is no report on the expression of P-gp across disease states or between sinus and adjacent intranasal sub sites. Therefore, the pattern and degree of epithelial P-gp expression was examined in three subject groups: the control subjects; the subjects having chronic sinusitis (CRS) without nasal polyposis; and the subjects having chronic sinusitis with nasal polyposis (CRSwNP).

Control subjects were defined as subjects free of rhinosinusitis. Subjects were defined as having CRS with or without NP using the established consensus diagnostic criteria (Rosenfeld et al., Otolaryngol Head Neck Surg. 2007 September; 137(3 Suppl):S1-31). Exclusion criteria included the following: use of steroids or immunotherapy within the preceding 4 weeks, aspirin sensitivity (ASA triad), ciliary dysfunction, autoimmune disease, cystic fibrosis or any known immunodeficiency. Tissues were collected from the septum, inferior turbinate, and paranasal sinuses (or polyp in CRSwNP) in each subject.

Following mucosal sampling, the tissues were immediately snap frozen in OCT. Four samples per subsite were sectioned at 10 μm and preserved in 4° C. acetone. Following blocking, the primary antibody (monoclonal anti-P-gp clone F4, 1:250, Sigma Aldrich, St. Louis, Mo.) was applied for 24 h at 4° C. The tissue was then rinsed followed by application of the secondary antibody (Anti-Mouse IgG (Fc specific) F(ab')2 fragment-FITC, 1:160, Sigma Aldrich, St. Louis, Mo.) for 30 minutes at room temperature. Slides were then rinsed and mounted in Vectashield containing propidium iodide (Vector Laboratories, Burlingame, Calif.) for nuclear counterstaining. Negative control slides were considered those in which the primary antibody was omitted from the staining procedure.

Quantitative fluorescent immunohistochemistry (Q-FIHC) for membranous P-gp expression was performed using previously described techniques (Kirkeby et al., J Immunol. Methods. 2005 June; 301(1-2):102-13). Briefly, standardized image capture was performed with an upright epifluorescent microscope (Carl Zeiss, Oberkochen, Germany) using the FITC filter following a standard 1000 ms exposure. Imaging sites were chosen based on morphology using the nuclear stain to eliminate the potential for bias. Images were then exported in tagged image file format (TIFF) into a graphics editing program (Adobe Photoshop v8.0, San Jose, Calif.). Images were cropped to exclude all non-tissue bearing regions. The lasso tool was used to partition the image into epithelial and stromal regions. The partitioning accuracy was verified using matched propidium iodide nuclear stained images. Following partitioning, the magic wand tool (tolerance 30) was used to select pixels exceeding the luminosity tolerance threshold in each compartment. Fluorescence in a relatively acellular region of the stromal compartment was considered non-specific background staining and used as an internal control for each slide. An average luminosity score reflecting the epithelial and stromal compartments was generated and an epithelial/stromal luminosity ratio was recorded for each slide.

For statistical analysis, the sample size of four subjects per subgroup was determined by a power analysis assuming a 1-β of 80% and a significance level of p<0.05. Staining ratios of 1 or less were considered negligible expression above background. The significance of differences between P-gp expression ratios was determined using a 2 tailed Student's t-test (SigmaStat v3.1, Systat Software Inc, San Jose, Calif.).

Figure 1:
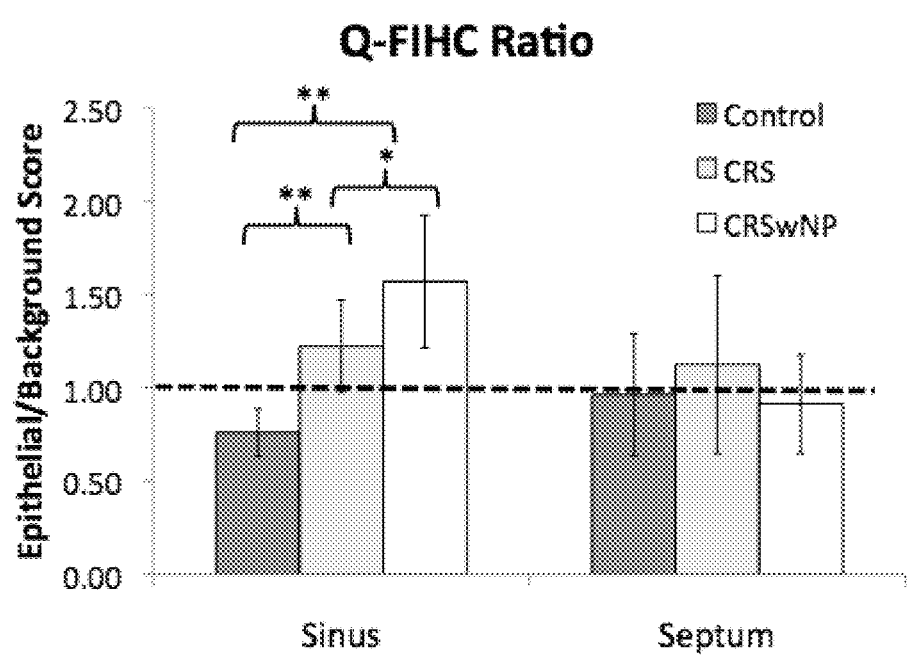
FIG. 1 is a bar graph showing Q-FIHC ratios of P-gp staining intensity at two tissue subsites (sinus and septum) among the control subject groups (Control), the subject group having chronic rhinosinusitis but without nasal polyps (CRS), and the subject group having chronic rhinosinusitis with nasal polyps (CRSwNP) (* p<0.001, ** p=0.002). Dashed line denotes a ratio of 1 suggesting no increased epithelial staining over background.

Among the sinus mucosal specimens, P-gp expression in the CRSwNP group (n=4, 1.570+/−0.354) was significantly greater than both the CRS group (n=4, 1.224+/−0.248) and the control group (n=4, 0.762+/−0.128) (p<0.001, p=0.002; respectively) (FIG. 1, 2). P-gp expression in the CRS group was significantly greater than the control group (p=0.002) (FIG. 1, 2). Among the negative control slides, there was no difference between the staining ratios of the CRSwNP, CRS, or control samples (0.889+/−0.125, 0.982+/−0.030, and 0.929+/−0.137, n=4, respectively).

Among the septal mucosal samples, there was no significant difference between CRSwNP (n=4, 0.914+/−0.264), CRS (n=4, 1.126+/−0.476), or control (0.966+/−0.327) tissues (FIG. 1). Among the inferior turbinate mucosal samples, there was no significant difference between CRSwNP (n=4, 1.047+/−0.157), CRS (n=4, 1.099+/−0.362), or control tissues (n=4, 0.824+/−0.181).

When examined under high magnification, P-gp staining in the CRSwNP and CRS samples was localized to both the apical and basolateral aspects of the epithelial cell membranes (FIG. 3).

These results show that membrane-bound P-gp protein expression was upregulated in the sinus epithelial cells in the subjects having CRSwNP or CRS relative to the control subjects. Within the same subjects, expression in adjacent non-diseased subsites was not similarly significantly elevated. Thus P-gp may play a role in the etiopathogenesis of rhinosinusitis.

Example 2

Membranous P-Glycoprotein is Expressed in the Primary Nasal Epithelial Cells The primary nasal epithelial cell cultures (PNECCs) were generated from the sinus mucosal biopsies from five subjects who are free of rhinosinusitis and undergoing surgery for either cerebrospinal fluid leak repair or tumor removal. Exclusion criteria included the following: diagnosis of chronic sinusitis, use of oral steroids or immunotherapy within the preceding 4 weeks, aspirin sensitivity, ciliary dysfunction, autoimmune disease, cystic fibrosis, or any known immunodeficiency. All tissues were derived from schneiderian mucosa within the middle meatus.

Mucosal biopsies were washed and digested in Pronase for 90 minutes at 37° C. Cell suspensions were separated from particulate matter by centrifugation and resuspended in basal epithelial growth medium (BEGM) (Lonza, Basel, Switzerland). Cells were plated for 2 hours on standard tissue culture plates to remove contaminating fibroblasts. Cells were then expanded for 3-5 days on collagen coated 75 cm² dishes (Corning Life Sciences, Corning, N.Y.). Once confluent, the PNECCs were trypsinized and re-seeded evenly on human collagen type IV-coated 6-well tissue culture plates. Cultures were grown to 80% confluence in BEGM prior to testing. PNECC cells intended for immunohistochemistry were grown on tissue culture treated coverslips placed within the wells.

PNECC cells were exposed to 23 hours of stimulation with lipopolysaccharide (LPS, 0.05 mg/mL), which is a toll-like receptor 4 agonist and capable of eliciting a strong immune responses. Control cells were considered those exposed to culture medium alone (BEGM). A 0.4% trypan blue (Sigma, St. Louis, Mo.) cell survival assay was used to ensure the stimulant exposures were not cytotoxic. In all wells, less than 20% of cells were stained blue indicating greater than 80% survival of the cells. Following the LPS exposures, the media was removed from each well.

Q-FIHC for membranous P-gp expression was performed using previously described techniques (Kirkeby et al., 2005). Briefly, PNECC cells were fixed in 4° C. acetone. Following blocking, the primary antibody (monoclonal anti-P-gp clone F4, 1:250, Sigma Aldrich, St. Louis, Mo.) was applied for 24 h at 4° C. The cells were then rinsed followed by application of the secondary antibody (Anti-Mouse IgG (Fc specific) F(ab')2 fragment-FITC, 1:160, Sigma Aldrich, St. Louis, Mo.) for 30 min at room temperature. The coverslips were then rinsed and mounted in Vectashield containing propidium iodide (Vector Laboratories, Burlingame, Calif.) for nuclear counterstaining. Negative control slides were considered those in which the primary antibody was omitted from the staining procedure. The mean corrected luminosity was considered the staining intensity (calculated using Image J v1.45s) divided by the total number of pixels subtended by the cells.

For statistical analysis, the sample size of five subjects was determined by a power analysis assuming a 1-β of 80% and a significance level of $p<0.05$. The significance of differences in membranous P-gp expression was determined using 2 tailed Student's t-tests with post-hoc testing using the Bonferroni procedure (SigmaStat v4, Systat Software Inc, San Jose, Calif.).

Figure 4:
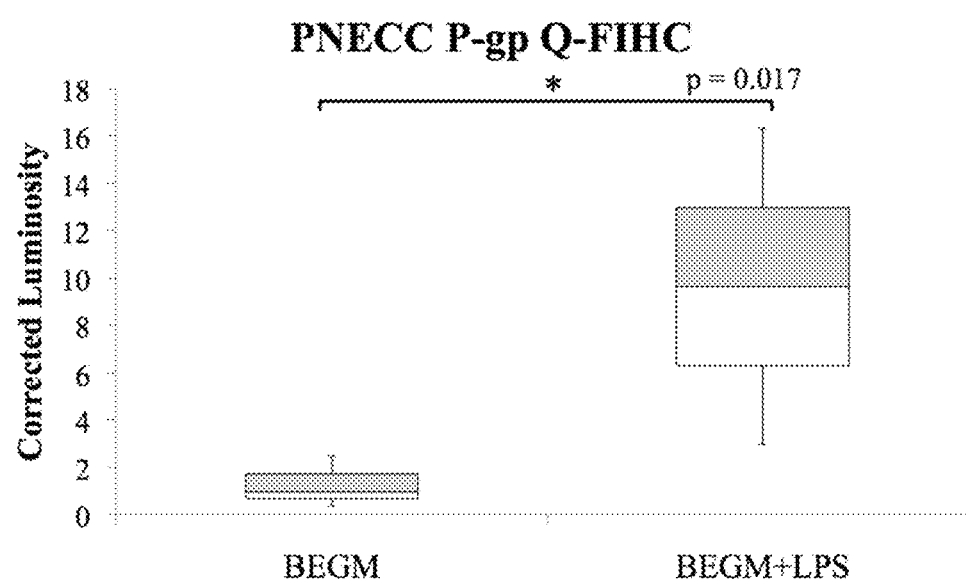
FIG. 4 is a graph showing Q-FIHC staining intensity of membranous P-gp in PNECCs exposed to culture media alone (BEGM) versus BEGM with 0.05 mg/mL of LPS for 23 hours (h). Corrected luminosity refers to the total luminosity divided by the total cell area per field. Exposure to LPS resulted in a significant increase in staining intensity.
Figure 5:
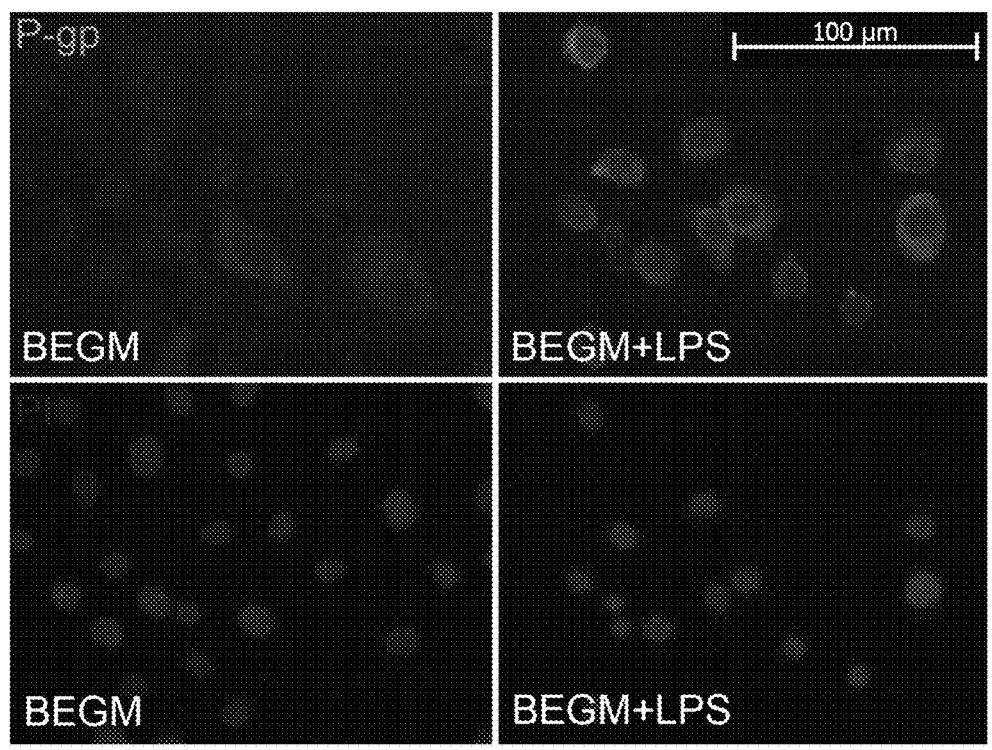
FIG. 5 is a set of fluorescent images in primary human sinonasal epithelial cell culture depicting P-gp staining (upper windows) following exposure to BEGM or BEGM+LPS. The lower windows depict the matched propidium iodide (PI) nuclear staining for cellular localization. P-gp staining intensity was quantified in FIG. 4.

Membranous P-gp was detected by Q-FIHC in submerged PNECCs grown in culture media alone (BEGM) with a mean corrected luminosity of 1.27 (95% CI 0.41 to 2.13). Exposure of PNECCs to 23 h of LPS resulted in a significant increase in P-gp expression with a mean corrected luminosity of 9.64 (95% CI 4.30 to 14.98, p=0.017) (FIGS. 4 and 5).

Figure 6:
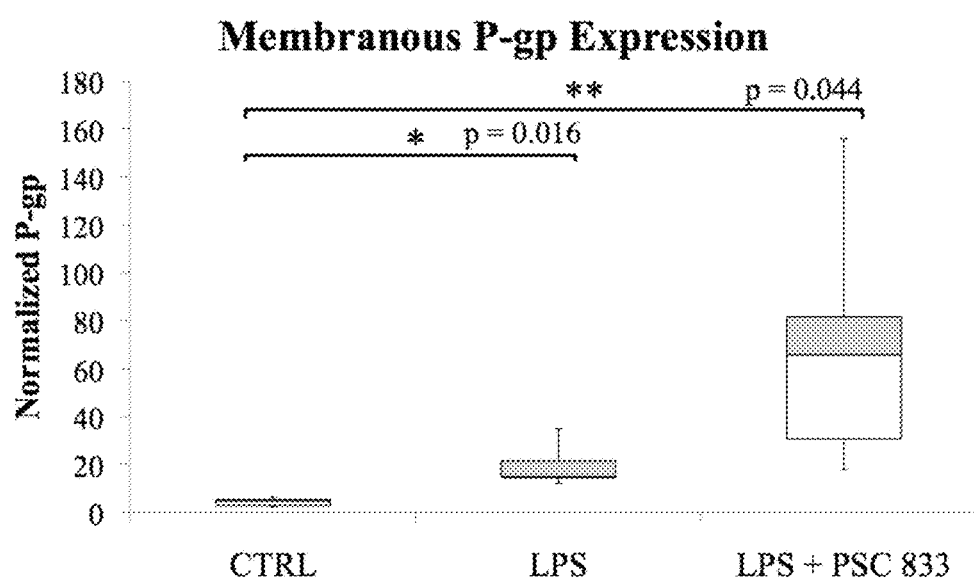
FIG. 6 is a box graph showing membranous P-gp expression determined by ELISA following membrane protein extraction. The significant increase in expression following LPS exposure was again seen confirming the findings by IHC. There was no significant difference in expression seen between cells exposed to LPS and those exposed to LPS along with a P-gp inhibitor (PSC 833, p=0.115).

This increase in P-gp expression was confirmed by ELISA following membrane extraction. Following removal of media from each well, the cytoplasmic and membranous protein fractions were isolated using a two-step extraction assay (DualXtract, Bulldog Bio, Inc., Portsmouth, N.H.). Membrane bound P-gp was quantified by subjecting the membranous fraction to ELISA (USCN Life Sciences Inc., Wuhan, P.R. China) and normalized to the cytoplasmic protein concentration. Normalized membranous P-gp was significantly greater in LPS-exposed PNECCs than in control cells (mean, 95% CI; 19.63, 11.62 to 27.64 vs. 4.42, 2.88 to 5.97, respectively, p=0.016) (FIG. 6).

The immunohistochemical and ELISA data show that P-gp was both present and functional within PNECC. The primary antibody used in our Q-FIHC study is specific to an extracellular loop of the P-gp protein providing further confirmation that our data reflects the activity of the membrane bound P-gp as opposed to the cytoplasmic fraction which does not participate in substrate transport out of the cell.

In some wells, a specific P-gp inhibitor (PSC 833 8micM, Tocris Bioscience, Bristol, UK) was applied to the cells 1 hour prior to LPS stimulation. Following the LPS and PSC 833 treatment, the media was removed from each well, and ELISA was performed to quantify membrane bound P-gp. LPS stimulated membranous P-gp did not change significantly when an 8micM PSC 833 solution was added as compared to LPS alone (70.40, 22.77 to 118.04; p=0.115) (FIG. 6).

Example 3

P-Glycoprotein is Responsive to Selective Inhibition In Vitro

The primary nasal epithelial cell cultures (PNECCs) were generated as previously described in Example 2. Specific P-gp inhibitors (PSC 833 8micM or 80micM, Tocris Bioscience, Bristol, UK; and verapamil 10micM or 100micM, Sigma, St. Louis, Mo.) were added to the culture medium for 21 hours. Verapamil is a first-generation P-gp inhibitor. PSC 833 is a "second-generation" P-gp specific inhibitor that lacks immunosuppressive activity. PSC 833 is thought to impair both the ATPase activity as well as the transport function of P-gp as a high affinity competitive substrate (Morjani et al., Methods Mol. Biol. 2010; 596:433-46).

Rhodamine 123 accumulation assay was then performed. Rhodamine 123 (500micM, Sigma, St. Louis, Mo.), a P-gp specific substrate, was then added to each well for 2 hours. The rhodamine 123 was then removed and the P-gp inhibitor alone was added back to the wells for 1 hour. The media was then removed and the cells were lysed using Cell Lytic M (Sigma, St. Louis, Mo.). The total intracellular rhodamine 123 concentration in each well was determined by spectrophotometry (excitation 510 nm, emission 534 nm) and normalized to the total cytoplasmic protein using a Pierce BCA Protein Assay Kit (Thermo Scientific, Waltham, Mass.). Retention of intracellular rhodamine 123 over baseline was considered proportional to degree of P-gp inhibition.

Figure 7:
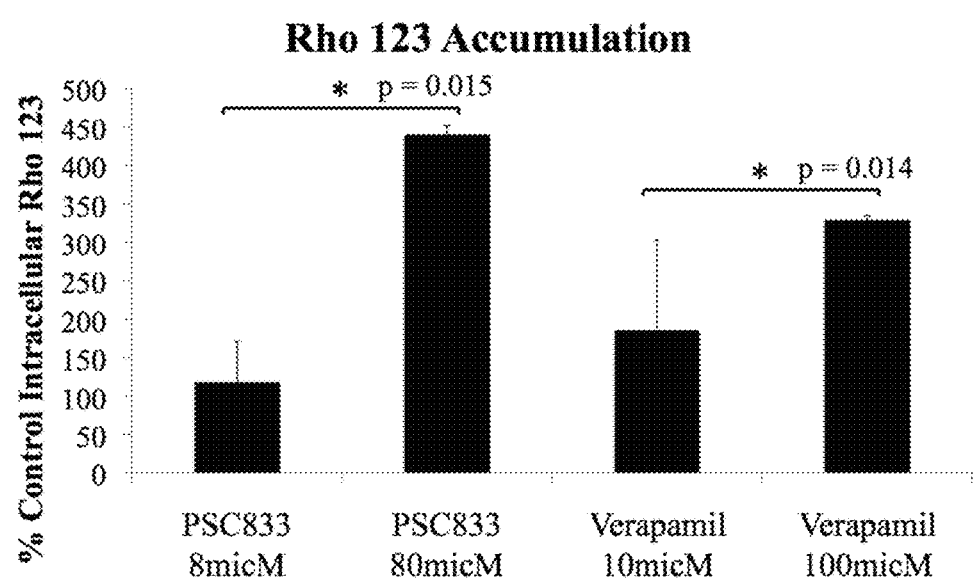
FIG. 7 is a bar graph of rhodamine 123 accumulation assay demonstrating concentration of intracellular rhodamine as compared to baseline following inhibition of P-gp using either PSC 833 or verapamil. The evident dose response using two separate inhibitors confirmed that the P-gp expressed in PNECCs is sensitive to inhibition. The accumulation in rhodamine 123 over baseline seen with 8micM of PSC 833 suggested that the alterations in cytokine secretion seen following PSC 833 exposure at this concentration may be directly attributable to P-gp inhibition.

The Rhodamine 123 accumulation assay shows that selective inhibition of P-gp led to a significant increase in intracellular rhodamine 123 over baseline in a dose-dependent fashion. Exposure to an 8micM solution of PSC 833 resulted in a mean 118.12+/−12.16% increase in accumulated P-gp while an 80micM demonstrated a significant mean increase of 439.46+/−117.59% (p=0.015) (FIG. 7). A similar dose-dependent accumulation was seen using a 10micM and 100micM verapamil solution (mean+/−SD, 185.33+/−6.59% vs. 328.27+/−66.98%, respectively, p=0.014) (FIG. 7).

The accumulation assay results show that the low dose PSC 833 utilized in this study was sufficient to inhibit P-gp mediated transport as evidenced by increased retention of intracellular rhodamine 123 over baseline. While the dose response seen suggests that P-gp is not fully inhibited at 8micM of PSC 833, the lower dose was utilized in the following cytokine secretion experiments to prevent the possibility of cytotoxicity.

Example 4

P-Glycoprotein Participates in Regulation of Stimulated Epithelial Cytokine Secretion In Vitro The primary nasal epithelial cell cultures (PNECCs) were generated as previously described in Example 2. Cells were exposed to 23 hours of stimulation with LPS (0.05 mg/mL) with or without concomitant P-gp inhibition by PSC 833 (8micM), which was applied to cells 1 hour prior to LPS treatment. Control wells were considered those exposed to culture medium alone (BEGM). A 0.4% trypan blue (Sigma, St. Louis, Mo.) cell survival assay was used to ensure the stimulant and inhibitor exposures were not cytotoxic. In all wells less than 20% of cells were stained blue indicating greater than 80% survival. Following the LPS and PSC 833 exposures, the media was removed from each well. Cytokine concentrations for IL-6, IL-8, GM-CSF, and TSLP in each well were determined by ELISA according to the manufacturer guidelines (eBioscience, San Diego, Calif.). Cytokine concentrations were normalized to total media protein concentrations using a Pierce BCA Protein Assay Kit.

Figure 8:
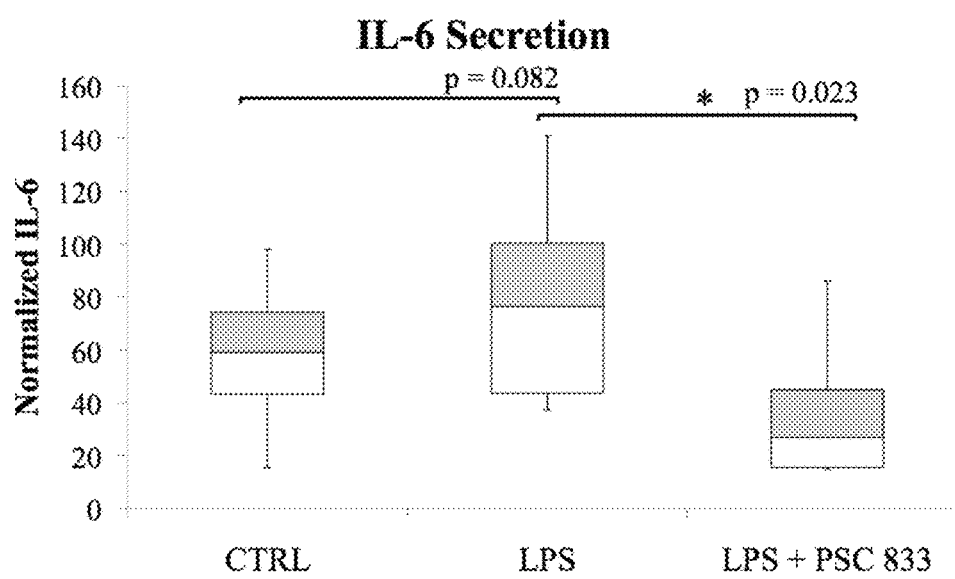
FIG. 8 is a box graph showing secreted IL-6 concentration (normalized to total media protein) in the control condition (CTRL) following exposure to culture media alone as compared to PNECCs exposed to media+LPS (0.05 mg/mL), and media+LPS (0.05 mg/mL)+PSC 833 (8micM). Note the significant reduction in LPS stimulated IL-6 secretion following inhibition of P-gp with PSC 833.

With respect to normalized IL-6, PNECCs demonstrated a detectable baseline secretion that was non-significantly upregulated following LPS stimulation (mean, 95% CI; 57.95, 30.58 to 85.37 vs. 79.67, 42.26 to 117.07, respectively, p=0.082). Stimulated IL-6 secretion was significantly decreased following P-gp inhibition (mean 37.60, 95% CI 11.54 to 63.65, p=0.023) (FIG. 8).

Figure 9:
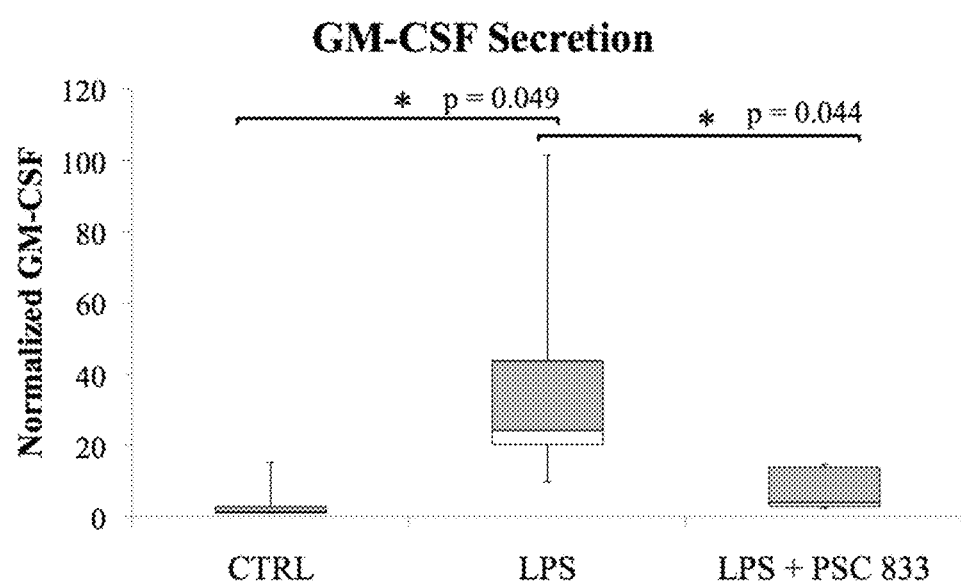
FIG. 9 is a box graph showing secreted GM-CSF concentration (normalized to total media protein) in the control condition (CTRL) following exposure to culture media alone as compared to PNECCs exposed to media+LPS (0.05 mg/mL), and media+LPS (0.05 mg/mL)+PSC 833 (8micM). Note the significant reduction in LPS stimulated GM-CSF secretion following inhibition of P-gp with PSC 833.

With respect to normalized GM-CSF, PNECCs demonstrated a detectable baseline secretion that was significantly upregulated following LPS stimulation (mean, 95% CI; 4.45, −0.88 to 9.77 vs. 39.92, 7.90 to 71.94, respectively, p=0.049). Stimulated GM-CSF secretion was significantly decreased following P-gp inhibition (mean 7.64, 95% CI 2.25 to 13.03, p=0.044) (FIG. 9).

Figure 10:
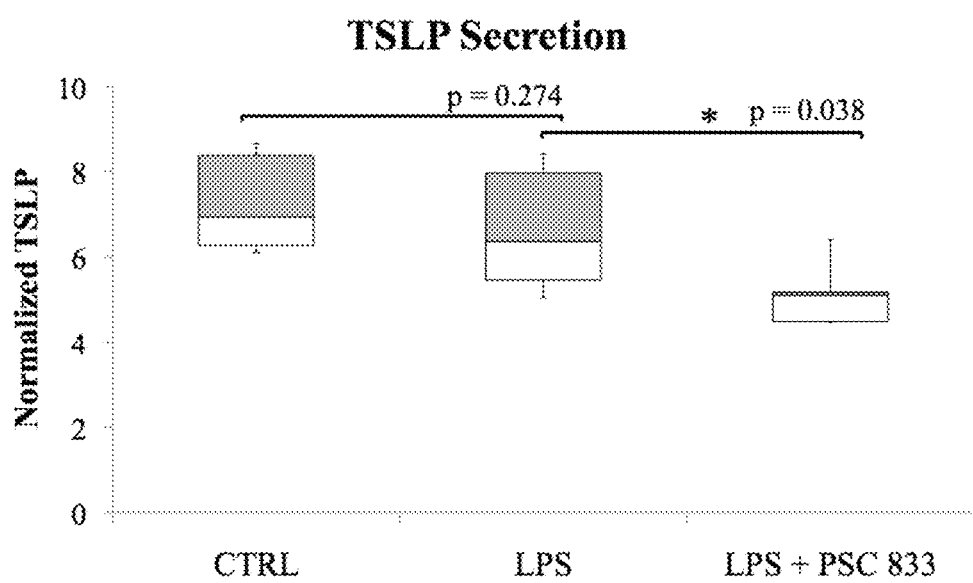
FIG. 10 is a box graph showing secreted TSLP concentration (normalized to total media protein) in the control condition (CTRL) following exposure to culture media alone as compared to PNECCs exposed to media+LPS (0.05 mg/mL), and media+LPS (0.05 mg/mL)+PSC 833 (8micM).

With respect to normalized TSLP, PNECCs demonstrated a detectable baseline secretion that was non-significantly upregulated following LPS stimulation (mean, 95% CI; 7.27, 6.23 to 8.30 vs. 6.65, 5.35 to 7.96, respectively, p=0.2'74). Stimulated TSLP secretion was significantly decreased following P-gp inhibition (mean 5.13, 95% CI 4.44 to 5.82, p=0.038) (FIG. 10).

With respect to normalized IL-8, PNECCs demonstrated a detectable baseline secretion that was significantly upregulated following LPS stimulation (mean, 95% CI; 263.81, 157.22 to 370.40 vs. 912.91, 466.89 1358.92, respectively, p=0.018). Stimulated IL-8 secretion demonstrated a trend towards reduction following P-gp inhibition although this was not significant (mean 801.09, 95% CI 596.88 to 1005.30, p=0.313) (FIG. 11).

Among the cytokines sensitive to PSC 833 exposure, the LPS stimulated secretion following P-gp inhibition was equivalent to or significantly less than baseline levels (IL-6, p=0.014; GM-CSF, p=0.001; TSLP, p=0.008).

The cytokine assays demonstrated that inhibition of P-gp resulted in a significant reduction in LPS stimulated IL-6, GM-CSF, and TSLP secretion. The lack of significant inhibition of IL-8 suggests that P-gp mediated immunomodulation is selective and does not apply to all secreted cytokines. The stable P-gp expression in LPS stimulated cells exposed to PSC 833 as compared to LPS alone suggests that the reduction effect cannot be attributed to a down-regulation in epithelial P-gp. The rhodamine 123 accumulation assay confirms that PSC 833 is mediating its effect through P-gp specific inhibition.

As demonstrated herein, P-glycoprotein is overexpressed in sinonasal inflammation. In addition, P-gp functions as an immunomodulator through regulation of epithelial cytokine secretion. P-gp therefore contributes to the etiopathogenesis of sinonasal inflammation.

Example 5

P-Glycoprotein Inhibition in Epithelial Cells Results in Increased Intracellular Steroid Retention and Potentiates the Anti-Inflammatory Effect of Steroid Primary sinonasal epithelial cells were obtained from three patients having chronic rhinosinusitis with nasal polyps, who were treated with steroid dexamethasone. These cultured primary sinonasal epithelial cells were stimulated with lipopolysaccharide (LPS) in the presence or absence of the P-gp inhibitor PSC 833. Treatment with PSC 833 resulted in increased intracellular dexamethasone retention relative to the cells treated with dexamethasone alone in all three patients (FIG. 12). The mean increase in the normalized dexamethasone retention was statistically significant by t-test (FIG. 12). Several steroids are known substrates of P-glycoprotein; a reduction in P-gp-mediated efflux results in increased retention of steroid, which may potentiate or sensitize the cells to the therapeutic effects of steroid.

The steroid retention effect was confirmed in nasal polyp explants (n=12/group) treated with two different corticosteroid (dexamethasone or prednisone) and two independent P-gp inhibitors (Verapamil or Zosuquidar). FIG. 13 illustrates the normalized intracellular corticosteroid concentration of nasal polyp explants after exposure to either dexamethasone (0.05 mg/mL) or prednisone (0.05 mg/mL) in the presence of media alone or the P-gp inhibitor Verapamil (12.5 μM) or Zosuquidar (0.31 μM). A statistically significant increase in intracellular prednisone retention was observed in the nasal polyp explants after exposure to either Verapamil or Zosuquidar (FIG. 13A). A statistically significant increase in intracellular dexamethasone retention was observed after Verapamil exposure (FIG. 13B). A similar trend of increase in intracellular dexamethasone retention was seen after Zosuquidar exposure (FIG. 13B).

The ability of nasal polyp explants to retain steroid after a 30-minute incubation in dexamethasone (0.05 mg/mL, n=6) was examined. Following incubation, polyp explants were placed either in media alone or in media containing the P-gp inhibitor PSC 833 (8 μM) and the amount of steroid released by the explants into the surrounding media was measured. A statistically significant decrease in steroid release was observed in explants exposed to PSC 833, relative to explants exposed to media alone (FIG. 14). These data indicate that blocking P-gp pump action prevents dexamethasone from being cleared by the cells and thereby enhances its therapeutic efficacy.

The increase in intracellular corticosteroid concentration potentiates its anti-inflammatory effect. Primary sinonasal epithelial cell culture was derived from patients with chronic sinusitis with nasal polyps (CRSwNP) and stimulated with LPS, a component of gram negative bacterial cell walls. FIG. 15 shows that the control cells that were not stimulated with LPS had very low baseline level of GM-CSF secretion, LPS (0.0125 mg/ml) treatment increased GM-CSF secretion. Treatment with P-gp inhibitor PSC833 (80 μM) and dexamethasone (0.1 mg/mL) reduced GM-CSF secretion in cells stimulated with LPS when compared to dexamethasone treatment alone (FIG. 14).

Example 6

P-Glycoprotein Promotes Epithelial Th2 Associated Cytokine Secretion in Chronic Sinusitis with Nasal Polyps Chronic sinusitis with nasal polyps (CRSwNP) is characterized by the presence edematous polypoid mucosa and eosinophilic inflammation (Chin D, Harvey R J., Curr. Opin. Otolaryngol. Head Neck Surg. 21: 23-30, 2013). While multiple etiologic hypotheses have been explored, recent evidence has focused on the sinonasal epithelial cell as a primary driver of the local dysregulated immune response through secretion of T-helper (Th)2 promoting cytokines (Sachse F, Becker K, von Eiff C, Allergy 65:1430-7, 2010; Damm M, Quante G, Rosenbohm J, Otolaryngol Head Neck Surg. 134:245-9, 2006). Although a role of P-gp in the etiopathogenis of CRSwNP has been suggested, its specific capability of modulating Th2 associated cytokines in nasal polyps has not been explored.

The sinonasal epithelium functions as a barrier organ against the external environment and is endowed with an array of innate and adaptive immunologic mechanisms to combat extrinsic pathogens (Lane A P, Truong-Tran Q A, Schleimer R P. Am J Rhinol. 20:138-44, 2006; Bachert C, Gevaert P, van Cauwenberge P., Allergy 57:480-7, 2002). While these local exposures may lead to mucosal inflammation, among patients with nasal polyps, the persistence of eosinophilic disease in the face of antimicrobial therapy suggests an alternate mechanism. Recent studies have demonstrated that the epithelial cell is capable of independently promoting Th2 inflammation in CRSwNP (Van Crombruggen K, Zhang N, Gevaert P, et al., J Allergy Clin Immunol 128:728-32, 2011). Olze et al. demonstrated that the eosinophil chemoattractants, Eotaxins 1, 2, and 3, are upregulated in nasal polyp tissue (Olze H, Förster U, Zuberbier T, Rhinology 44:145-50, 2006). Subsequent in vitro studies have localized eotaxin to epithelial cells and have demonstrated that both eotaxin 3 and acidic mammalian chitinase (AMCase), another pro-Th2 mediator, are upregulated in response to exposure to chitin (Lalaker A, Nkrumah L, Lee W K, et al. Am J Rhinol Allergy 23:8-14, 2009). Exposure to *Staphylococcus aureus* has also been shown to induce IL-6 production in nasal polyp derived epithelial cells. This is postulated to promote Th2 activity by counteracting IL-10 induced regulatory T-cell suppression (Sachse F, Becker K, von Eiff C, Allergy 65:1430-7, 2010; Damm M, Quante G, Rosenbohm J, Otolaryngol Head Neck Surg. 134:245-9, 2006).

While these studies suggest that epithelial cells are capable of orchestrating a local immune response, the post-translational mechanisms governing cytokine secretion are less understood. The classic or canonical pathway involves cytosolic translocation of cytokine precursors to the endoplasmic reticulum (ER) under the direction of a signal peptide. Non-canonical pathways have also been described which may confer greater selective control over cytokine release into the tissue microenvironment (Nickel W., Eur. J Biochem. 270:2109-19, 2003).

P-gp mediated cytokine regulation represents an established non-canonical pathway which has been reported in a variety of tissues including, T-cells (Kooij G, Backer R, Koning J J, PLoS One 4:e8212, 2009), Schwann cells (Marty V, Medina C, Combe C, Glia 49:511-9, 2005), and the HCT16 and HCT116 colon carcinoma cell lines (Stein U, Walther W, Shoemaker R H., Br J Cancer 74:1384-91, 1996). The previous examples demonstrate that a significant reduction in several Th2-associated cytokines following selective P-gp inhibition in lipopolysaccharide (LPS)-stimulated epithelial cultures derived from healthy mucosa; and that the epithelial P-gp was overexpressed in nasal polyps relative to control tissue. Taken together, these findings suggest a potential role for P-gp in the etiopathogenesis of CRSwNP. The capability of P-gp in modulating epithelial derived Th2 associated cytokine secretion in nasal polyps was therefore explored.

Sinus mucosal biopsies were procured from subjects who met the 2012 EPOS16 criteria for chronic sinusitis with nasal polyps. Exclusion criteria included the following: use of topical/oral steroids or immunotherapy within the preceding 4 weeks, aspirin sensitivity, ciliary dysfunction, autoimmune disease, cystic fibrosis, or any known immunodeficiency.

Immediately following harvest of nasal polyp and septal mucosal samples in 4 patients, tissue explants were cut into 3×3 mm cubes and incubated for 30 min at 37° C. in basal epithelial growth medium (BEGM) (Lonza, Basel, Switzerland) with or without 8 µM of the P-gp inhibitor PSC 833 (Tocris Bioscience, Bristol, UK). Calcein Acetoxymethylester (AM) 2.5 µM (BD Biosciences, Franklin Lakes, N.J.), a P-gp specific substrate, was then added to each sample and incubated for an additional 15 min at 37° C. All tissue was then snap frozen, sectioned, and imaged using excitation and emission filters of 467-498 nm and 513-556 nm, respectively for 500 ms. The epithelial and background luminosity was calculated using Image J (v1.45s). A corrected epithelial luminosity was calculated by dividing the epithelial and background values to normalize any variability in sample preparation or image capture.

Human sinonasal nasal epithelial cell cultures (HSNECCs) from five patients were grown from nasal polyps as previously described. Briefly, polyp samples were washed and digested in Pronase for 90 minutes at 37° C. Cell suspensions were separated from particulate matter by centrifugation and resuspended in BEGM. Cells were plated for 2 hours on standard tissue culture plates to remove contaminating fibroblasts. Cells were then expanded for 3-5 days on collagen coated 75 $cm^2$ dishes (Corning Life Sciences, Corning, N.Y.). Once confluent, the HSNECCs were trypsinized and re-seeded evenly on human collagen type IV-coated 6-well and 96-well tissue culture plates. 6-well cultures were grown to 80% confluence in BEGM prior to cytokine and protein analysis. 96-well plates intended for the dose dependent inhibition assay were grown to 100% confluence. Cells intended for immunohistochemistry were grown on tissue culture treated coverslips.

Membrane-bound P-glycoprotein in HSNECCs was quantified as follows. After removal of media from each well, the cytoplasmic and membranous protein fractions were isolated using a two-step extraction assay (DualXtract, Bulldog Bio, Inc., Portsmouth, N.H.). Membrane-bound P-gp was quantified by subjecting the membranous fraction to ELISA (USCN Life Sciences Inc., Wuhan, P.R. China) and normalized to the total cytoplasmic protein concentration using a Pierce BCA Protein Assay Kit (Thermo Scientific, Waltham, Mass.).

Fluorescent immunohistochemistry (FIHC) for membranous P-gp expression was performed as described above. Briefly cells were fixed in 4° C. acetone. Following blocking, the primary antibody (monoclonal anti-P-glycoprotein clone F4, 1:250, Sigma Aldrich, St. Louis, Mo.) was applied for 24 h at 4° C. The tissue was then rinsed followed by application of the secondary antibody (Anti-Mouse IgG (Fc specific) F(ab')2 fragment-FITC, 1:160, Sigma Aldrich, St. Louis, Mo.) for 30 minutes at room temperature. The coverslips were then rinsed and mounted in Vectashield containing propidium iodide (Vector Laboratories, Burlingame, Calif.) for nuclear counterstaining. Negative control slides were considered those in which the primary antibody was omitted from the staining procedure.

PSC 833 dose-dependent inhibition assay was performed as follows. PSC 833 was added to confluent HSNECC cultures in a 96-well plate at concentrations ranging from 0-1.25 µM. Following incubation for 30 minutes at 37° C., 2.5 µM of calcein AM was added for an additional 15 minutes. Cells were then washed with cold PBS and the total intracellular calcein concentration in each well was determined by fluorescent spectrophotometry (excitation 494 nm, emission 517 nm). Retention of intracellular calcein relative to the uninhibited control wells was considered proportional to P-gp inhibition.

The sample size was determined by a power analysis assuming a 1-β of 80% and a significance level of $p<0.05$. The significance of differences between P-gp activity in mucosal explants, normalized cytokine secretion, and membranous P-gp expression were determined using a nonparametric, two-tailed, Mann-Whitney U test. The correlation between LPS stimulated cytokine secretion and membranous P-gp expression was determined using a Pearson product-moment correlation coefficient. The differences P-gp inhibition using PSC 833 were determined using a one tailed Mann-Whitney U test.

Following incubation of both nasal polyp and septal explants (n=4, each) in media containing calcein AM (2.5 µM), no significant difference in intraepithelial calcein retention as measured by epithelial corrected luminosity was found between sites (mean+/−SD; 2.55+/−0.62 vs. 2.32+/−0.86; respectively; p=NS). Among the septal explants, no significant change in calcein retention was seen following P-gp inhibition with 8 µM PSC 833 (2.22+/−0.92). Among the nasal polyps explants, P-gp inhibition resulted in a significant increase in intraepithelial calcein retention as compared to the uninhibited samples (5.17+/−1.76; p<0.05) (FIG. 16). Thus epithelial P-gp is hyperfunctional in nasal polyps as compared to adjacent non-polypoid mucosa.

These findings demonstrated a rise in intraepithelial calcein in polyp as compared to septal explants following inhibition with a P-gp specific inhibitor PSC 833. This suggests that P-gp activity in polyps is focally increased relative to adjacent healthy mucosa (Morjani H, Madoulet C. Methods Mol Biol 596:433-46, 2010; Iqbal M, Gibb W, Matthews S G. Endocrinology 152:1067-79, 2011). Example 1 showed that the presence of membranous P-gp overexpression in CRSwNP as compared to non-diseased subsites. This assay therefore provides supporting evidence suggesting that this overexpression is also associated increased pump activity in nasal polyps.

P-gp was detected in the membrane extract of all CRSwNP HSNECCs by ELISA (n=5). The mean normalized concentration in cells exposed to LPS 0.05 mg/mL (22.23+/−10.22) was significantly greater than in cells exposed to media alone (5.91+/−3.15, p<0.05). The presence of membranous P-gp expression was confirmed by FIHC using a primary antibody targeted to the extracellular loop of P-gp (FIG. 17).

Calcein fluorescence in confluent HSNECCs (n=5) increased in a dose-dependent manner following exposure to successively higher concentrations of PSC 833 (FIG. 18). The percent fluorescence relative to uninhibited control wells at 1.25 µM PSC 833 (134.32+/−43.78) was significantly greater than at 0.31 µM (89.07+/−28.56; p=0.04) but not at 0.63 µM (102.58+/−44.32; p=NS) (FIG. 18).

For P-gp mediated cytokine secretion testing, HSNECC cells were exposed to 0.05 mg/mL LPS stimulation for 23 hours with or without concomitant P-gp inhibition using PSC 833 (8 µM), which was applied one hour prior to LPS stimulation. Control wells were considered those exposed to culture medium alone (BEGM). A 0.4% trypan blue (Sigma, St. Louis, Mo.) cell survival assay was used to ensure the stimulant and inhibitor exposures were not cytotoxic. In all wells less than 20% of cells were stained blue indicating greater than 80% survival. Following the LPS and PSC 833 exposures, the media was removed from each well. Cytokine concentrations for GM-CSF, IL-6, IL-8, and IL-25 in each well were determined by ELISA according to the manufacturer guidelines (GM-CSF, IL-6, IL-8 eBioscience, San Diego, Calif.; IL-25 Assay Biotechnology, San Francisco, Calif.). Cytokine concentrations were normalized to total media protein concentrations using a Pierce BCA Protein Assay Kit.

The basal secretion of GM-CSF (pcg/mL) normalized to total media protein (mcg/mL) was 4.33+/−1.12. Exposure to LPS 0.05 mg/mL resulted in a significant increase in secretion (45.21+/−41.39; p<0.01) which was significantly inhibited by the addition of PSC 833 8 µM (8.47+/−3.28; p<0.01). The concentration of LPS stimulated GM-CSF secretion was highly correlated with the degree of membranous P-gp expression (r=0.824, p<0.05) (FIG. 19).

The basal secretion of IL-6 (pcg/mL) normalized to total media protein (mcg/mL) was 71.15+/−44.93. Exposure to LPS 0.05 mg/mL did not significantly alter IL-6 secretion (63.16+/−36.37, p=NS). The addition of PSC 833 8 µM significantly inhibited LPS stimulated IL-6 secretion (39.94+/−31.07; p<0.05). The concentration of LPS stimulated IL-6 secretion was highly correlated with the degree of membranous P-gp expression (r=0.833, p<0.05) (FIG. 19).

The basal secretion of IL-8 (pcg/mL) normalized to total media protein (mcg/mL) was 316.47+/−174.42. Exposure to LPS 0.05 mg/mL resulted in a significant increase in secretion (1041.17+/−550.52; p<0.05). No inhibition of IL-8 secretion was seen following the addition of PSC 833 8 µM (1608.41+/−471.94). The concentration of LPS stimulated IL-8 secretion did not correlate with the degree of membranous P-gp expression (r=−0.011, p=NS) (FIG. 20).

The basal secretion of IL-25 (pcg/mL) normalized to total media protein (mcg/mL) was 0.031+/−0.019. Exposure to LPS 0.05 mg/mL resulted in a significant increase in secretion (0.075+/−0.039; p<0.05). No inhibition of IL-25 secretion was seen following the addition of PSC 833 8 µM (0.073+/−0.038; p=NS). The concentration of LPS-stimulated IL-25 secretion did not correlate with the degree of membranous P-gp expression (r=0.008, p=NS) (FIG. 20).

The majority of chronic sinusitis with nasal polyps is associated with eosinophilic infiltration and a predominantly Th2 cytokine profile (Mjosberg J M, Trifari S, Crellin N K, Nat. Immunol. 12:1055-62, 2011). Multiple lines of evidence suggest that the respiratory epithelial cell is capable of elaborating a variety of cytokines such as IL-6, IL-25, IL-33, TSLP, and GM-CSF which can not only activate Th2 cells (Peters A T, Kato A, Zhang N, J Allergy Clin Immunol 125:397-403, 2010; Reh D D, Wang Y, Ramanathan M Jr, Am J Rhinol Allergy 24:105-9, 2010; Wisniewski J A, Borish L. Allergy Asthma Proc 32:83-94, 2011), but may also stimulate the recently described type 2 innate lymphoid cell (ILC) to produce T-cell independent Th2 polarizing cytokines (Mjösberg J M, Trifari S, Crellin N K, Nat. Immunol. 12:1055-62, 2011). Despite these findings, a complete understanding of the mechanisms responsible for maintaining the chronic inflammation seen in CRSwNP remains elusive. Non-canonical regulation of epithelial cytokine secretion via P-gp may represent one such mechanism.

Primary sinonasal epithelial cell culture model derived from nasal polyps was utilized to further explore the immunomodulatory role of P-gp. The FIHC and ELISA findings confirmed that membranous P-gp expression both persisted in vitro and was subject to active regulation following TLR4 stimulation with LPS. The in vitro P-gp inhibition assay also confirmed that P-gp remained sensitive to PSC 833 in a dose dependent manner and was subject to inhibition at concentrations well below those utilized in the cytokine secretory studies. These results validate the use of the HSNECC model in examining P-gp functionality and suggest that any changes seen in cytokine release following PSC 833 exposure may be directly attributable to impairment of P-gp pump activity.

The findings that IL-6 and GM-CSF secretion are reduced following inhibition with PSC 833 suggest that their release into the local polyp microenvironment is subject to P-gp mediated regulation. This is further supported by the correlation between P-gp expression and secretion among these cytokines. Interestingly, this effect seems to be cytokine specific as both IL-8 and IL-25 release occurred independently of P-gp inhibition or expression.

The presence of an in vitro correlation between P-gp expression and cytokine secretion coupled with the in vivo findings of P-gp overexpression and hyperactivity in nasal polyps suggests that P-gp may play a central role in promoting and maintaining chronic inflammation in CRSwNP. This is further supported by the fact that both IL-6 and GM-CSF are associated with Th2 inflammation, a key feature of CRSwNP. IL-6 has previously been reported to be elevated in CRSwNP, is known to activate Th17 cells, and may contribute to the insufficiency of regulatory T-cells in nasal polyps (Peters A T, Kato A, Zhang N, Allergy Clin. Immunol. 125:397-403, 2010). Similarly GM-CSF has been shown to be capable of activating eosinophils in CRSwNP leading to enhanced eosinophil chemotaxis and prolonged survival (Shin S H, Lee S H, Jeong H S, Laryngoscope 113:1374-7, 2003).

While the pathogenesis of CRSwNP remains elusive, the epithelial cell has gained attention as a primary driver of the Th2 inflammation which characterizes the disease. These data suggest that P-gp overexpression may promote non-canonical Th2 associated epithelial cytokine secretion in nasal polyps. These findings provide a framework for maintaining chronic inflammation in CRSwNP and offer a potential therapeutic target. In light of this novel role for P-gp as an upper respiratory tract immunomodulator, future efforts will be directed at elucidating the mechanism of P-gp overexpression in the setting of CRSwNP.

Example 7

P-Glycoprotein is a Marker of Tissue Eosinophilia and Radiographic Inflammation in Chronic Rhinosinusitis without Nasal Polyps Chronic rhinosinusitis (CRS) represents a heterogeneous group of diseases with a variety of pathophysiologic mechanisms. A broad division between chronic sinusitis with and without nasal polyps (CRSwNP and CRSsNP, respectively) serves as a widely accepted distinction secondary to phenotypic differences evident clinically. The immunologic profiles underlying these disease states suggest that a broader spectrum exists with a predominantly eosinophilic profile subtending not only patients with CRSwNP but a subset of those with CRSsNP as well. The presence of eosinophilic chronic sinusitis (ECRS) is clinically relevant as these patients share not only the immunologic profile of those with CRSwNP but also the propensity for greater symptom severity and worse outcomes.

Eosinophilic chronic rhinosinusitis represents a histologic diagnosis consisting of mucosal eosinophilia evident in biopsy specimens. While the precise definition of ECRS may be debated, Soler has demonstrated that a cut point of >10 eosinophils per hpf provided the best correlation with patient outcomes (Soler Z M, Sauer D, Mace J, et al. Otolaryngol Head Neck Surg. 142(1):64-71, 2010). ECRS has also been shown in multiple studies to correlate with worse symptoms (Sun D I, Joo Y H, Auo H J, et al., Eur Arch Otorhinolaryngol. 266(7):981-6, 2009; Soler Z M, Sauer D A, Mace J, et al., Otolaryngol Head Neck Surg. 141(4):454-61, 2009; Lee T J, Liang C W, Chang P H, et al., Auris Nasus Larynx. 36(6):655-60, 2009), lower airway hyperactivity (Amorim M M, Araruna A, Caetano L B, et al., Clin Exp Allergy. 2010; 40(6):867-74; Han D H, Kim S W, Cho S H, et al., Allergy 64(1):118-22, 2009), and poor surgical outcomes (Soler, 2010). These findings may be understood in the context of a shared T-helper 2 (Th2)-skewed immunologic profile as patients with frank nasal polyps (Takeno S, Hirakawa K, Ishino T. Allergol Int. 59(3):247-56, 2010). A parsimonious interpretation of these findings suggests that ECRSsNP and CRSwNP may reflect different phenotypic manifestations of the same etiologic process.

P-gp has been previously demonstrated to participate in non-canonical cytokine secretion in T-cells (Drach J, Gsur A, Hamilton G, et al., Blood. 88(5):1747-54, 1996). The overexpression of P-gp in CRSwNP coupled with its ability to promote cytokine secretion suggests that it may play a role in the pathogenesis of the eosinophilic inflammation seen in nasal polyps. Given the relationship between CRSwNP and ECRS, P-gp expression in patients with ECRSsNP was compared to that in patients with CRSsNP.

Sinus mucosal biopsy samples were harvested from the anterior ethmoid sinus of patients having chronic rhinosinusitis. Exclusion criteria included the following: use of oral steroids or immunotherapy within the preceding 4 weeks, aspirin sensitivity (ASA triad), ciliary dysfunction, autoimmune disease, cystic fibrosis or any known immunodeficiency. Patient with focal etiologies for sinusitis including mucoceles, odontogenic sources, and fungal balls were similarly excluded from the study.

Following mucosal sampling, the tissue was stained as previously described. Briefly, following blocking, the primary antibody (monoclonal anti-p-glycoprotein clone F4, 1:250, Sigma Aldrich, St. Louis, Mo.) was applied for 24 h at 4° C. The tissue was then rinsed followed by application of the secondary antibody(Anti-Mouse IgG (Fc specific) F(ab')2 fragment-FITC, 1:160, Sigma Aldrich, St. Louis, Mo.) for 30 min at room temperature. Slides were then rinsed and mounted in Vectashield containing propidium iodide (PI) for nuclear counterstaining. Negative control slides were considered those in which the primary antibody was omitted from the staining procedure.

Fluorescent staining intensity was quantified using a modification of previously described methods (Bleier B S., Int Forum Allergy Rhinol. 2(2):122-5, 2012). Briefly, image capture was performed with an upright epifluorescent microscope following a standard 1000 ms exposure. Images were then exported into Image J (v1.45s). The nuclear stain was used to select both the epithelium and a non-tissue bearing background region generating a staining intensity ratio. Samples were excluded if the epithelial staining intensity in the negative control slide exceeded that of the adjacent stroma. An epithelial/background staining ratio greater than or equal to 3 was defined as high P-gp expression. This threshold or cut point was derived from pilot data demonstrating P-gp expression ratios of less than 3 in nasal septal mucosa, a region with a previously described low level of basal P-gp epithelial expression.

For each patient, a representative hematoxylin and eosin slide generated as part of their routine pathologic analysis at surgery was selected. The number of eosinophils per five 400× high powered fields (hpf) were recorded by two independent and blinded observers as previously described (Soler Z M, Sauer D, Mace J, et al. Otolaryngol Head Neck Surg. 142(1):64-71, 2010). The values were averaged to generate a mean eosinophil per hpf score for each patient. Radiographic inflammation was quantified by a single blinded observer using the Lund-Mackay staging system.

P-gp expression ratios, tissue eosinophilia, and radiographic scores between the patient groups were compared with a two tailed Student's t-test using R (v2.15.2, 2012). P values <0.05 were considered statistically significant.

Among the 39 patients included in the study, the epithelial/background ratio of the high expression group (mean+/−SD, 4.86+/−1.33, n=7 or 17.95%) was significantly greater than that of the low expression group (1.91+/−0.45, n=32 or 82.05%, p<0.001) (FIG. 21A). While there was a relative predominance of females in the high P-gp expression group, there were no significant differences between the two groups with respect to patient age or race (Table 1).

TABLE 1

Patient demographics

|  | Low expression | High expression |
|---|---|---|
| Age (years) | 47.8 ± 16.7 | 44.3 ± 14.8 |
| Female (%) | 50 | 85.7 |
| Male (%) | 50 | 14.3 |
| Caucasian (%) | 87.5 | 85.7 |
| Minority (%) | 12.5 | 14.3 |

Among the high P-gp expression group, all patients demonstrated greater than 10 eosinophils/hpf with a mean of 62.38 (range 10.0-240.6). The low P-gp expression group demonstrated a mean of 5.11 eosinophils/hpf (range 0.0-41.4) which was significantly lower than that of the high expression group (p=0.0003) (FIG. 21B).

The mean Lund-Mackay score was significantly greater among the high P-gp expression group than that of the low P-gp expression group (11.86+/−2.79 vs. 6.84+/−4.19; p=0.005) (FIG. 21C).

FIGS. 22 A and B are fluorescent immunohistochemical images of mucosa depicting representative (A) low epithelial P-gp expression and (B) high epithelial P-gp expression. FIGS. 22 C and D are matched high powered (400×) H&E stromal images depicting the absence (C) and presence (D) of mucosal eosinophilia (black arrows denote individual eosinophils). FIGS. 22 E and F are coronal CT scans demonstrating increased radiographic inflammation in the patient with high P-gp expression (F) relative to the patient with low P-gp expression (E).

These data demonstrate that among patients with CRSsNP, P-gp overexpression predicts tissue eosinophilia. While the mechanistic relationship between epithelial P-gp and eosinophilic inflammation remains unclear, the common finding of upregulation in both CRSwNP and ECRS lends support to the idea that P-gp may play an etiopathologic role. Although the clinical utility of Lund-Mackay score may be debated, one of its strengths is that it provides an objective reflection of the degree of global inflammation present in the patient. As with CRSwNP, the intraluminal disease burden seen in patients with ECRS tends to be more severe involving most if not all of the sinuses. In non-eosinophilic patients, disease may be more isolated to a specific region leading to a lower overall Lund-Mackay score even if the local inflammation is quite severe. Consequently, we chose to utilize the Lund-Mackay score as an additional surrogate marker of inflammation which served to support our histologic findings.

In summary, eosinophilic chronic rhinosinusitis shares a similar clinical and histologic profile with CRSwNP, suggesting the two may represent different manifestations of the same underlying process. In Examples 1-6, P-gp was shown to be overexpressed in CRSwNP and is capable of modulating epithelial cytokine secretion. Here the data showed that P-gp is similarly overexpressed in ECRS and is associated with radiologic evidence of increased inflammation. These findings further strengthen the link between ECRS and CRSwNP and suggest the potential for an etiopathologic role for P-gp in both diseases.

Example 8

Osteitis is Associated with P-Glycoprotein Overexpression in Patients with Chronic Sinusitis without Nasal Polyps Chronic rhinosinusitis (CRS) associated with T-helper cell type 2 (Th2) inflammation has been increasingly recognized as a distinct phenotype characterized by eosinophilic infiltration. The immunologic profiles underlying this disease state suggests that eosinophilic chronic rhinosinusitis without nasal polyps (ECRS) and chronic sinusitis with nasal polyps (CRSwNP) may exist along a spectrum of Th2 mediated mucosal inflammation. These patients tend to manifest more severe symptoms and worse outcomes following medical and surgical management. Example 7 showed that P-glycoprotein(P-gp) overexpression has been found in both patients with ECRS and CRSwNP and is capable of promoting Th2 associated cytokine secretion. Identification of patients with elevated P-gp may therefore be useful to guide treatments directed toward this novel therapeutic target. Radiographic osteitis scores have been previously shown to correlate with eosinophilic inflammation and thus may be useful in stratifying patients with P-gp overexpression (Snidvongs K, McLachlan R, Chin D, et al. Rhinology 2012; 50:299-305; Snidvongs K, McLachlan R, Sacks R, et al. Int Forum Allergy Rhinol 2013; 3:369-375).

Examples 1-6 showed that P-gp functions as an immunomodulator capable of regulating the efflux of cytokines from its host cell, and suggested that P-gp may play a role in the pathogenesis of Th2 mediated sinonasal inflammation. Identification of patients with altered P-gp expression may therefore provide prognostic information as well as offer a novel therapeutic target.

Tissue remodeling is a molecular process of formation and resorption leading to transient or permanent changes in structure of tissue. In CRS, tissue remodeling is exhibited in both mucosa and bone, characterized by osteitis, mucosal hypertrophy, fibrosis, and thickening of the basement membrane. Osteitis involves inflammatory changes in the underlying bone that lead to persistence of disease and is increasingly recognized as playing a significant role in recalcitrant CRS (Detwiller K Y, Smith T L, Mace J C, et al. Int Forum Allergy Rhinol 3:364-368, 2013). Snidvongs et al. demonstrated that both the Kennedy Osteitis (KOS) and Global Osteitis Scores (GOS) were capable of predicting disease severity in eosinophilic inflammation (Snidvongs K, McLachlan R, Sacks R, Int Forum Allergy Rhinol 3:369-375, 2013). Thus, whether these osteitis scores can be used as a non-invasive clinical marker of P-gp overexpression in patients with CRS was examined.

Sinus mucosal biopsy samples were procured from 38 patients having CRS. CRS was defined using the established consensus diagnostic criteria. Tissue was harvested from the anterior ethmoid sinus of each patient. Exclusion criteria included the following: The presence of nasal polyposis, use of oral steroids or immunotherapy within the preceding 4 weeks, aspirin sensitivity (ASA triad), ciliary dysfunction, autoimmune disease, cystic fibrosis, or any known immunodeficiency. Patient with focal etiologies for sinusitis including mucoceles, odontogenic disease, and fungal balls were similarly excluded from the study. Demographic data was recorded.

Following mucosal sampling, the tissue was stained using quantitative fluorescent immunohistochemistry as previously described. Briefly, following blocking, the primary and secondary antibodies were added for 24 h and 30 minutes, respectively followed by the addition of the nuclear counterstain. Negative control slides were considered those in which the primary antibody was omitted from the staining procedure. Fluorescent staining intensity was quantified using previously described methods. An epithelial/background staining ratio ≥3 was defined as high P-gp expression. This cut point was derived from prior studies demonstrating a correlation between staining ratios ≥3 and mucosal eosinophilia in the setting of CRS.

For patient demographics, among the 38 patients included in study, the epithelial/background ratio of the high expression group (mean±SD, 4.86±1.33; n=7; 18.42%) was significantly greater than that of the low expression group (1.93±0.45; n=31; 81.57%; p<0.001) (FIG. 23A). While there was a relative predominance of females in the high P-gp expression group, there were no significant differences between the two groups with respect to patient age or race. No patients in the high P-gp expression group had undergone prior surgery while seven (22.6%) patients in the low P-gp expression group were undergoing revision procedures (Table 2).

TABLE 2

Patient Demographics

|  | High P-gp expression group | Low P-gp expression group |
| --- | --- | --- |
| Age (years) | 40.43 ± 12.07 | 48.52 ± 16.43 |
| Female (%) | 51.61 | 85.71 |
| Male (%) | 14.29 | 48.39 |
| Caucasian (%) | 85.71 | 87.10 |
| Minority (%) | 14.29 | 12.9 |
| Prior surgery (%) | 0 | 22.6 |

Peripheral blood eosinophil counts were available in 25 patients. Eosinophil concentrations were reported as an auto differential result (normal 0-6%) using a Sysmex XS-1000i (Kobe, Japan) instrument. The methodology of the instrument for the differential is light scatter and fluorescent emission.

Serum eosinophilia was defined as having serum percent eosinophils greater than 6%. Patients with high P-gp expression had higher median serum eosinophil counts (mean±SD, 6.98±2.17) than the low P-gp expression group (2.36±1.38, p<0.001) (FIG. 23B).

The Kennedy osteitis score (KOS) is determined by using computed tomography (CT) to diagnose osteitis based on the thickness of bony partitions in the maxillary, ethmoid, and sphenoid sinuses (Lee J T, Kennedy D W, Palmer J N, Am J Rhinol 20:278-282, 2006). Thickness of bony partitions were measured and classified into the following categories of osteitis severity: mild (<3 mm); moderate (4-5 mm); and severe (>5 mm). This was modified to create a summary score so that comparable assessments could be made to the Global osteitis score (GOS) (Georgalas C, Videler W, Freling N, Clin Otolaryngol 35:455-461, 2010). All 10 sinuses (right and left frontal, anterior ethmoid, posterior ethmoid, maxillary, and sphenoid) were scored as being 0 (<3 mm), 1 (3-5 mm) or 2 (>5 mm) with total scores ranging from 0 to 20. Woven bone with thickened, irregular, heterogeneous lining of the sinus walls were measured rather than normal lamellar/cortical bony wall.

The presence of osteitis was also scored by using the Global osteitis score (GOS) system proposed by Georgalas (Georgalas C, Videler W, Freling N, Clin Otolaryngol 35:455-461, 2010) and modified by Snidvongs (Snidvongs K, McLachlan R, Sacks R, Int Forum Allergy Rhinol 2013; 3:369-375). Osteitis was defined as loss of bone definition, hyperostosis, new bone formation, or signal heterogeneity overlying each sinus wall. Bony walls of the paranasal sinuses were scored ranging from 0 to 4 making the total score of 0 to 40 as previously described (Lee J T, Kennedy D W, Palmer J N, et al. Am J Rhinol 2006; 20:278-282.). All CT scans were reviewed by a single observer blinded to P-gp expression and serum eosinophil levels.

Global and Kennedy Osteitis scores were compared using a Pearson correlation coefficient. Correlation(r) values from 0.7-1 were considered strongly correlated. Osteitis scores and serum eosinophil concentrations between P-gp expression groups were compared using a non-parametric Mann-Whitney U test (two-tailed). P values <0.05 were considered statistically significant.

Both the GOS and KOS were significantly higher among patients with P-gp overexpression. Among patients with high P-gp expression, the GOS and KOS values (mean±SD, 15.86±4.91 and 6.29±1.25, respectively) were significantly greater than those in the low P-gp expression group (4.55±4.33 and 2.23±1.71, p<0.001) (FIG. 24 A, B). When the two scoring systems were compared to each other, there was a significant correlation between KOS and GOS values (r=0.835, p<0.001) (FIG. 24C).

Eosinophilic chronic rhinosinusitis (ECRS) is a subtype of recalcitrant CRS characterized by a T-helper cell type 2 skewing of the local inflammatory milieu. While the etiology of ECRS and Th2 inflammation is unclear, multiple studies have pointed to epithelial cell as a key participant in the inflammatory cascade (Ferguson B J. Curr Opin Otolaryngol Head Neck Surg 12:237-242, 2004; Mehta V, Campeau N G, Kita H, et al. Mayo Clin Proc 83:671-678, 2008). Examples 1-7 demonstrated that membranous epithelial P-glycoprotein is overexpressed in both CRSwNP and ECRS and is capable of promoting secretion of Th2 associated cytokines. These findings suggest that P-gp may play an important etiopathologic role.

The first large series to report on the association of disease severity and eosinophilia in CRS was published by Newman (Newman L J, Platts-Mills T A, Phillips C D, JAMA 271:363-367, 1994). Multiple subsequent reports consistently demonstrated that eosinophilia is a marker for more extensive disease that is more refractory to surgical cure (Zadeh M H, Banthia V, Anand V K, Am J Rhinol 16:313-317, 2002; Szucs E, Ravandi A, Goossens A, Am J Rhinol 16:131-134, 2002). Given these findings, a method of identifying these patients preoperatively would be of considerable value. Osteitis as measured by the two separate scoring systems was shown to correlate with tissue eosinophilia (Snidvongs K, McLachlan R, Sacks R, Int Forum Allergy Rhinol 3:369-375, 2013). This study was designed to determine whether osteitis could similarly predict P-gp overexpression.

FIG. 24C confirmed that KOS and GOS are highly correlated and thus both represent an acceptable method of quantifying osteitis. More importantly, FIGS. 24A and 24B showed that a greater osteitis burden is associated with P-gp overexpression among patients with chronic rhinosinusitis without nasal polyps. FIG. 23 showed that patients with high P-gp expression also had higher median serum eosinophil counts than the low expression group suggesting that Th2 skewed inflammation may be implicated as a common link of this relationship.

A potential confounding factor in quantitating bony remodeling is that osteitis is likely multifactorial and previous studies have suggested that surgery itself may play a role in increasing the incidence of osteitis (Georgalas C. Curr Opin Otolaryngol Head Neck Surg 21:45-49, 2013; Cho S H, Shin K S, Lee Y S, Am J Rhinol 22:537-541, 2008; Georgalas C, Videler W, Freling N, Clin Otolaryngol 35:455-461, 2010). However, all patients in the high P-gp expression group were undergoing primary surgery and thus, at least in this population, surgery can be excluded as a source of osteitic remodeling.

In summary, P-glycoprotein overexpression in Th2 inflammation represents a recently described phenomenon which may play an important role in the etiopathogenesis of eosinophilic CRS. A method of predicting this patient population based on objective clinical criteria may be of value to help to stratify patients for the purposes of tailoring medical and surgical therapy as well as providing counseling on expectations following treatment. The data demonstrated that increased osteitis burden among unoperated patients is associated with higher P-gp expression. The presence of greater serum eosinophilia in the high P-gp expression group suggest that Th2 inflammation may play a role and further studies elaborating the mechanism by which P-gp overexpression and osteitis are associated are warranted.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating chronic rhinosinusitis in a subject, the method comprising:
    identifying a subject having chronic rhinosinusitis;
    administering to the subject an effective amount of a P-glycoprotein inhibitor,
    wherein the P-glycoprotein inhibitor is not an antibiotic agent, an antifungal agent, a corticosteroid, or a first generation P-glycoprotein inhibitor compound.

2. The method of claim 1, wherein the subject has chronic rhinosinusitis and nasal polyps.

3. The method of claim 1, wherein the P-glycoprotein inhibitor decreases P-glycoprotein expression in the subject's sinonasal epithelial cells.

4. The method of claim 1, wherein the P-glycoprotein inhibitor is administered systemically.

5. The method of claim 1, wherein the P-glycoprotein inhibitor is administered locally to the subject's nasal passage and sinuses.

6. The method of claim 5, wherein the P-glycoprotein inhibitor is delivered to the subject's nasal passage and sinuses by an inhalation device, by flushing, or by spraying.

7. The method of claim 5, wherein the P-glycoprotein inhibitor is administered to the subject by a P-glycoprotein inhibitor eluting implant surgically placed in the subject's nasal passage or sinuses.

8. The method of claim 7, wherein the P-glycoprotein inhibitor eluting implant is bioabsorbable.

9. The method of claim 1, wherein the subject having chronic rhinosinusitis was identified by endoscopy.

10. The method of claim 1, wherein the subject having chronic rhinosinusitis was identified by computed tomography.

11. The method of claim 1, wherein the subject having chronic rhinosinusitis was identified by observing the subject's symptoms and duration of symptoms.

12. The method of claim 1, further comprising monitoring the efficacy of the treatment by endoscopy.

13. The method of claim 1, further comprising monitoring the efficacy of the treatment by computed tomography.

14. The method of claim 1, further comprising monitoring the efficacy of the treatment by observing the subject's symptoms and duration of symptoms.

15. The method of claim 1, further comprising surgically removing any nasal polyps present in the subject.

16. The method of claim 1, wherein the P-glycoprotein inhibitor is administered in combination with one or both of a corticosteroid and an antibiotic.

17. The method of claim 16, wherein the corticosteroid is selected from dexamethasone, prednisone, prednisolone, triamcinolone, cortisol, budesonide, mometasone, fluticasone, flunisolide, and betamethasone.

18. The method of claim 1, wherein the P-glycoprotein inhibitor is administered in combination with a corticosteroid and an antibiotic.

19. A kit for treating chronic rhinosinusitis in a subject, said kit comprising
    a pharmaceutical composition comprising an effective amount of a P-glycoprotein inhibitor, wherein the P-glycoprotein inhibitor is not an antibiotic agent, an antifungal agent, a corticosteroid, or a first generation P-glycoprotein inhibitor compound; and
    a device for delivering the pharmaceutical composition to the subject's nasal passage and sinuses, wherein the device delivers the pharmaceutical composition to the subject's nasal passage and sinuses in a liquid, nebulized, or aerosolized form.

20. The kit of claim 19, further comprising a corticosteroid.

21. The kit of claim 19, further comprising an antibiotic.

* * * * *